US007371503B2

(12) United States Patent
Miyamatsu et al.

(10) Patent No.: US 7,371,503 B2
(45) Date of Patent: May 13, 2008

(54) SULFONIUM SALT COMPOUND, PHOTOACID GENERATOR, AND POSITIVE-TONE RADIATION-SENSITIVE RESIN COMPOSITION

(75) Inventors: Takashi Miyamatsu, Tokyo (JP); Hirokazu Niwata, Tokyo (JP); Satoshi Ebata, Tokyo (JP); Yong Wang, Tokyo (JP)

(73) Assignee: JSR Corporation, Tokyo (JP)

( * ) Notice: Subject to any disclaimer, the term of this patent is extended or adjusted under 35 U.S.C. 154(b) by 272 days.

(21) Appl. No.: 10/543,092

(22) PCT Filed: Jan. 9, 2004

(86) PCT No.: PCT/JP2004/000130

§ 371 (c)(1),
(2), (4) Date: Jul. 22, 2005

(87) PCT Pub. No.: WO2004/065377

PCT Pub. Date: Aug. 5, 2004

(65) Prior Publication Data

US 2006/0141383 A1 Jun. 29, 2006

(30) Foreign Application Priority Data

Jan. 22, 2003 (JP) ............................ 2003-013294
Jul. 4, 2003 (JP) ............................ 2003-271015

(51) Int. Cl.
*G03F 7/004* (2006.01)
*C07D 331/04* (2006.01)
*C07D 333/46* (2006.01)
*C07D 335/04* (2006.01)

(52) U.S. Cl. .................. 430/270.1; 430/905; 430/910; 430/922; 549/13; 549/29; 549/88; 549/90; 568/27; 568/28

(58) Field of Classification Search ............ 430/270.1, 430/905, 910, 922; 549/13, 29, 88, 90; 568/27, 568/28
See application file for complete search history.

(56) References Cited

U.S. PATENT DOCUMENTS

| | | | | |
|---|---|---|---|---|
| 5,919,596 | A | 7/1999 | Hedrick et al. | 430/270.1 |
| 6,187,504 | B1 * | 2/2001 | Suwa et al. | 430/270.1 |
| 6,908,722 | B2 * | 6/2005 | Ebata et al. | 430/270.1 |
| 2005/0266336 | A1 * | 12/2005 | Kodama | 430/270.1 |
| 2005/0287473 | A1 * | 12/2005 | Kodama | 430/270.1 |

FOREIGN PATENT DOCUMENTS

| | | | |
|---|---|---|---|
| DE | 100 54 550 | A1 | 5/2001 |
| EP | 0 849 634 | A1 | 6/1998 |
| GB | 1235815 | | 6/1971 |
| JP | 2002-229192 | | 8/2002 |

OTHER PUBLICATIONS

H. Bosshard, "5. Über die Anlagerung von Thioäthern an Chinone und Chinonimine in Stark sauren Medien," Helvetica Chimica Acia, vol. 55, No. 1, pp. 32-37 (1972).

* cited by examiner

*Primary Examiner*—John S. Chu
(74) *Attorney, Agent, or Firm*—Merchant & Gould, P.C.; Christopher W. Raimund

(57) ABSTRACT

A sulfonium salt compound excelling in transparency to deep ultraviolet rays at a wavelength of 220 nm or less, exhibiting well-balanced excellent performance such as sensitivity, resolution, pattern form, LER, and storage stability when used as a photoacid generator, a photoacid generator comprising the sulfonium salt compound, and a positive-tone radiation-sensitive resin composition containing the photoacid generator.

The sulfonium salt compound is shown by the following formula (I), (I)

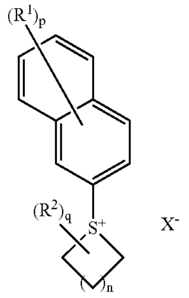

wherein $R^1$ represents a halogen atom, an alkyl group, a monovalent alicyclic hydrocarbon group, an alkoxyl group, or —$OR^3$ group, wherein $R^3$ is a monovalent alicyclic hydrocarbon group, $R^2$ represents a (substituted)-alkyl group or two or more $R^2$ groups form a cyclic structure, p is 0-7, q is 0-6, n is 0-3, and $X^-$ indicates a sulfonic acid anion.

The positive-tone radiation-sensitive resin composition comprises (A) a photoacid generator of the sulfonium-salt compound and (B) an acid-dissociable group-containing resin.

20 Claims, 6 Drawing Sheets

$^1$H-NMR spectrometry spectrum of the sulfonium salt (A-1)

$^1$H-NMR spectrometry spectrum of the sulfonium salt (A-2)

$^1$H-NMR spectrometry spectrum of the sulfonium salt (A-3)

$^1$H-NMR spectrometry spectrum of the sulfonium salt (A-4)

$^1$H-NMR spectrometry spectrum of the sulfonium salt (A-5)

$^1$H-NMR spectrometry spectrum of the sulfonium salt (A-6)

SULFONIUM SALT COMPOUND, PHOTOACID GENERATOR, AND POSITIVE-TONE RADIATION-SENSITIVE RESIN COMPOSITION

TECHNICAL FIELD

The present invention relates to a novel sulfonium salt compound suitable as a photoacid generator used in a positive-tone radiation-sensitive resin composition useful for microprocessing using various types of radiation, in particular, such as deep ultraviolet radiation, electron beams, and X-rays, a photoacid generator comprising the sulfonium salt compound, and a positive-tone radiation-sensitive resin composition containing the photoacid generator.

BACKGROUND ART

In the field of microfabrication represented by fabrication of semiconductor devices, a microfabrication technology enabling fabrication with a line width of less than 0.20 μm has been demanded to cope with the recent trend of high integration.

Use of light sources emitting a shorter wavelength light can be mentioned as a method for attaining such miniaturization of patterns. In these days, a KrF excimer laser (wavelength: 248 nm), an ArF excimer laser (wavelength: 193 nm), an $F_2$ excimer laser (wavelength: 157 nm), and EUV (wavelength: 13 nm, etc.) are more abundantly used instead of conventional light sources such as a g-line and i-line.

In regard to the photoresist material used with such light sources emitting a shorter wavelength light, it is difficult for a photoresist containing a novolac resin and naphthoquinone diazido conventionally used with a g-line or i-line to form fine patterns because of formation of tapered patterns due to strong absorption in the deep ultraviolet ray region. Moreover, since this type of photoresist exhibits only a low sensitivity of no more than 1, in terms of a quantum yield, the life of the excimer laser oscillation gas is short in the photo reaction during exposure to light. This causes a problem in the life of a lens, when the lens is used with a photoresist by which the lens is easily damaged by the excimer laser.

As a photoresist suitable for an excimer laser solving these problems, many chemically-amplified photoresists comprising a resin which causes a chemical reaction accompanied by change in solubility in a developer in the presence of an acid catalyst and a photoacid generator which generates an acid upon exposure with light have been proposed.

A widely known typical example of such a chemically-amplified photoresist for a KrF excimer laser comprises a resin containing polyhydroxystyrene in which the phenolic hydroxyl groups are protected by acid-dissociable groups such as an acetal group and t-butoxy carbonyl group and a photoacid generator such as a triaryl sulfonium salt represented by a triphenylsulfonium salt (Japanese Patent Application Laid-open No. 59-45439, for example).

The resin having the polyhydroxystyrene as a base skeleton used for a KrF excimer laser is not suitable as a chemically-amplified photoresist for an ArF excimer laser because of the strong absorption of light at a wavelength of 193 nm. Resin components such as a (meth)acrylate resin having an alicyclic skeleton, a polymer of norbornene derivatives having an alicyclic skeleton in the main chain, and a copolymer of a norbornene derivative and a maleic anhydride have been proposed as a chemically-amplified photoresist for an ArF excimer laser. On the other hand, a triaryl sulfonium salt, when used as a photoacid generator even in a comparatively small amount, reduces radiation transmittance of a resist due to the strong absorption by aromatic rings, even if the above resins are used as a resist. For this reason, the resist has problems in its performance such as difficulty in obtaining high resolution and formation of tapered pattern shape, unless the amount is unduly limited. The triaryl sulfonium salt thus is not always a suitable photoacid generator when an ArF excimer laser is used as radiation.

To overcome the problem of the triaryl sulfonium salt due to its low radiation transmittance, Japanese Patent Application Laid-open No. 2001-354669, for example, proposed other sulfonium salts such as a sulfonium salt containing a 2-oxoalkyl group. This type of sulfonium salt, however, significantly decreases sensitivity although transparency to radiation is remarkably improved. Therefore, practical sensitivity cannot always be obtained. Moreover, when the amount of the additive to improve the anti-basic property of the photoresist or the selection of the additive is not appropriate, the storage stability of the photoresist is impaired.

Japanese Patent Application Laid-open No. 10-232490 discloses a photoacid generator of a cyclic sulfonium salt containing a substituted or unsubstituted naphthyl group and a radiation-sensitive resin composition containing the photoacid generator. The transmissivity of the sulfonium salt having this-type of structure at a wavelength of 220 nm is disclosed. The resist was confirmed to exhibit excellent sensitivity and pattern shape when an ArF excimer laser was used, and to have good storage stability. However, since many of these compounds have an absorption peak near the wavelength of 193 nm, the effect of the absorption on radiation transmittance cannot be neglected when used in a chemically-amplified photoresist to be exposed to an ArF excimer laser. The amount of the compound that can be added is limited. Moreover, cyclic sulfonium salts, particularly those having a sulfur atom directly bonded to the α-position of a naphthyl group, tend to be decomposed by a dark reaction accompanied by a ring-opening reaction due to the steric hindrance of the naphthyl group, thus causing a problem in respect to storage stability of the resist solutions.

DISCLOSURE OF THE INVENTION

An object of the present invention is to provide a sulfonium salt compound excelling in transparency to deep ultraviolet rays at a wavelength of 220 nm or less, exhibiting well-balanced excellent performance such as sensitivity, resolution, pattern form, line edge roughness (hereinafter referred to as "LER"), storage stability, and the like when used as a photoacid generator, a photoacid generator comprising the sulfonium salt compound, and a positive-tone radiation-sensitive resin composition containing the photoacid generator.

As a result of synthesis and detailed performance evaluation of various sulfonium salt compounds which have not been conventionally synthesized, the present inventors have found that a sulfonium salt compound containing a naphthalene ring of which the β-position is bonded by a sulfur atom exhibits excellent transparency to light with a wavelength of 220 nm or less and can overcome the above-mentioned problems in prior art technologies when used as a radiation-sensitive resin composition. These findings have led to the completion of the present invention.

The above object can be achieved in the present invention by a sulfonium salt compound (hereinafter referred to as "sulfonium salt compound (I)" represented by the following formula (I):

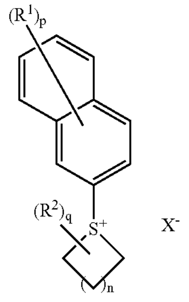

(I)

wherein $R^1$ represents a halogen atom, a linear or branched alkyl group having 1-14 carbon atoms, a monovalent hydrocarbon group having an alicyclic skeleton and containing 3-14 carbon atoms, a linear or branched alkoxyl group having 1-14 carbon atoms, a group represented by —$OR^3$ (wherein $R^3$ is a monovalent hydrocarbon group having an alicyclic skeleton and containing 3-14 carbon atoms), a linear or branched alkyl sulfanyl group having 1-14 carbon atoms, an organic sulfanyl group having an alicyclic skeleton and containing 3-14 carbon atoms, a linear or branched alkane sulfonyl group having 1-14 carbon atoms, or an organic sulfonyl group having an alicyclic skeleton and containing 3-14 carbon atoms, two or more $R^1$ groups that may present being either the same or different, $R^2$ represents a substituted or unsubstituted, linear, branched, or cyclic alkyl group having 1-14 carbon atoms, or two or more $R^2$ groups bond to form a monocyclic structure having 3-14 carbon atoms or a polycyclic structure having 6-14 carbon atoms, two or more $R^2$ groups that may present being either the same or different, p is an integer of 0-7, q is an integer of 0-6, n is an integer of 0-3, and $X^-$ represents a sulfonic acid anion.

The above object can be further achieved in the present invention by a photoacid generator (hereinafter referred to as "photoacid generator (AI)") comprising the sulfonium salt compound (I).

The above object can be further achieved in the present invention by a positive-tone radiation-sensitive resin composition comprising (A) a photoacid generator containing the photoacid generator (AI) as an essential component and (B) an acid-dissociable group-containing resin which is insoluble or scarcely soluble in alkali, but becomes alkali soluble when the acid-dissociable group dissociates.

BEST MODE FOR CARRYING OUT THE INVENTION

Figure 1:
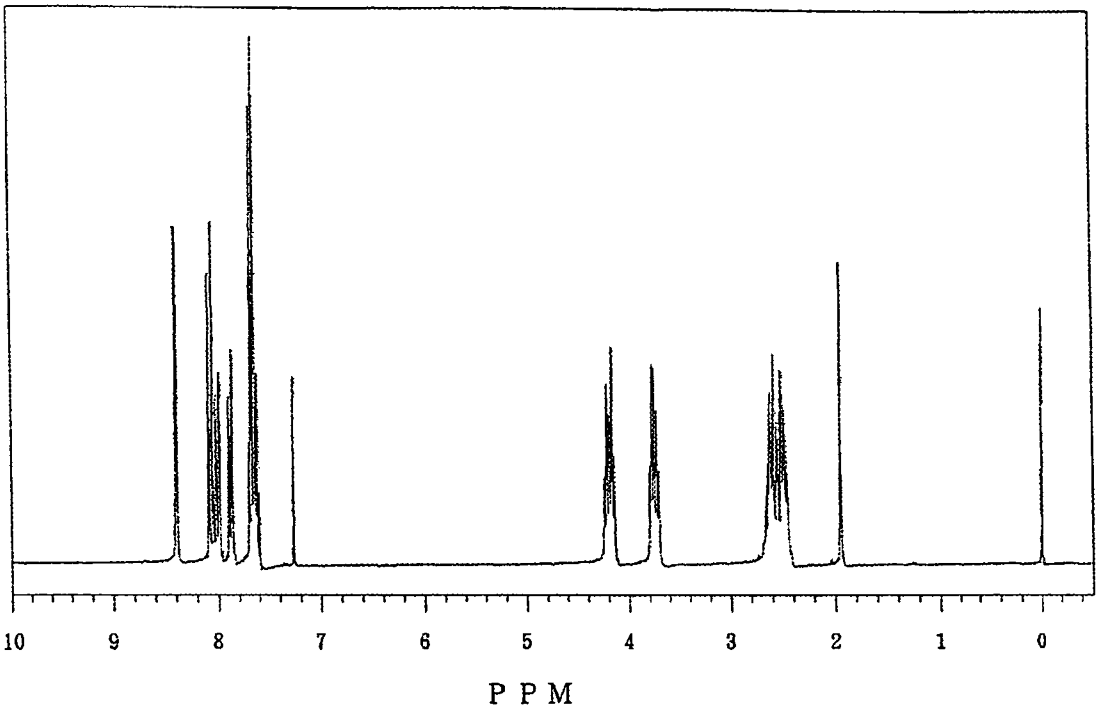
FIG. 1 shows a $^1$H-NMR spectrometry spectrum of the sulfonium salt (A-1).

The present invention will be described in more detail below.

Sulfonium Salt Compound (I):

As examples of the halogen atom represented by $R^1$ in the formula (1), a fluorine atom, chlorine atom, bromine atom, and iodine atom can be given.

As a linear or branched alkyl group having 1-14 carbon atoms represented by $R^1$, a methyl group, ethyl group, n-propyl group, i-propyl group, n-butyl group, 2-methylpropyl group, 1-methylpropyl group, t-butyl group, n-pentyl group, n-hexyl group, n-heptyl group, n-octyl group, n-nonyl group, n-decyl group, n-undecyl group, n-dodecyl group, t-dodecyl group, n-tridecyl group, n-tetradecyl group, and the like can be given.

As the monovalent hydrocarbon group having an alicyclic skeleton and containing 3-14 carbon atoms, a cycloalkyl group such as a cyclopropyl group, cyclobutyl group, cyclopentyl group, or cyclohexyl group; a group having an alicyclic ring originating from a bridged alicyclic hydrocarbon such as norbornane, bicyclo[2.2.2]octane, tricyclodecane, tetracyclododecane, or adamantane; a group obtainable by bonding of a methylene group or an alkylene group having 2-8 carbon atoms (for example, an ethylene group, a propylene group, etc.) with these cycloalkyl groups or the alicyclic ring (provided that the methylene group or alkylene group bonds with the naphthalene group of the formula (I)); and the like can be given.

As examples of the linear or branched alkoxyl group having 1-14 carbon atoms represented by $R^1$, a methoxy group, ethoxy group, n-propoxy group, i-propoxy group, n-butoxy group, 2-methylpropoxy group, 1-methylpropoxy group, t-butoxy group, n-pentyloxy group, n-hexyloxy group, n-heptyloxy group, n-octyloxy group, n-nonyloxy group, n-decyloxy group, n-undecyloxy group, n-dodecyloxy group, t-dodecyloxy group, n-tridecyloxy group, and n-tetradecyloxy group can be given.

As $R^3$ in the —$OR^3$ group represented by $R^1$, a cycloalkyl group such as a cyclopropyl group, cyclobutyl group, cyclopentyl group, or cyclohexyl group; a group having an alicyclic ring originating from a bridged alicyclic hydrocarbon such as norbornane, tricyclodecane, bicyclo[2.2.2]octane, tetracyclododecane, or adamantane; a group obtainable by bonding of a methylene group or an alkylene group having 2-8 carbon atoms (for example, an ethylene group, a propylene group, etc.) with these cycloalkyl groups or the alicyclic ring (provided that the methylene group or alkylene group bonds with the oxygen atom of the —$OR^3$ group); and the like can be given.

As the linear or branched alkyl sulfanyl group having 1-14 carbon atoms represented by $R^1$, a methyl sulfanyl group, ethyl sulfanyl group, n-propyl sulfanyl group, i-propyl sulfanyl group, n-butyl sulfanyl group, 2-methylpropyl sulfanyl group, 1-methylpropyl sulfanyl group, t-butyl sulfanyl group, n-pentyl sulfanyl group, n-hexyl sulfanyl group, n-heptyl sulfanyl group, n-octyl sulfanyl group, n-nonyl sulfanyl group, n-decyl sulfanyl group, n-undecyl sulfanyl group, n-dodecyl sulfanyl group, n-tridecyl sulfanyl group, n-tetradecyl sulfanyl group, and the like can be given.

As the organic sulfanyl group having an alicyclic skeleton and containing 3-14 carbon atoms represented by $R^1$, cycloalkyl sulfanyl groups such as a cyclopropyl sulfanyl group, cyclobutyl sulfanyl group, cyclopentyl sulfanyl group, and cyclohexyl sulfanyl group; organic sulfanyl groups in which the sulfur atom directly bonds to an alicyclic ring originating from a bridged alicyclic hydrocarbon such as (bicyclo[2.2.1]heptan-2-yl)sulfanyl group, (bicyclo[2.2.2]octan-2-yl)sulfanyl group, (tetracyclo [4.2.0.$1^{2.5}$.$1^{7.10}$]dodecan-3-yl)sulfanyl group, (adamantan-2-yl)sulfanyl group; organic sulfanyl groups obtainable by bonding of a methylene group or an alkylene group having 2-8 carbon atoms (for example, an ethylene group, a propylene group, etc.) with a cycloalkane such as cyclopropane, cyclobutane, cyclopentane, and cyclohexane or an alicyclic ring originating from a bridged alicyclic hydrocarbon such as norbornane, bicyclo[2.2.2]octane, tricyclodecane, tetracyclododecane, and adamantane (provided that the methylene group or alkylene group bonds to a sulfur atom); and the like can be given.

As the linear or branched alkane sulfonyl group having 1-14 carbon atoms represented by $R^1$, a methane sulfonyl group, ethane sulfonyl group, n-propane sulfonyl group, n-propane-2-sulfonyl group, n-butane sulfonyl group, 2-methylpropane-1-sulfonyl group, 1-methylpropane-1-sulfonyl group, 2-methylpropane-2-sulfonyl group, n-pentane sulfonyl group, n-hexane sulfonyl group, n-heptane sulfonyl group, n-octane sulfonyl group, n-nonane sulfonyl group, n-decane sulfonyl group, n-undecane sulfonyl group, n-dodecane sulfonyl group, n-tridecane sulfonyl group, n-tetradecane sulfonyl group, and the like can be given.

As the organic sulfonyl group having an alicyclic skeleton and containing 3-14 carbon atoms represented by $R^1$, cycloalkyl sulfonyl groups such as a cyclopropyl sulfonyl group, cyclobutyl sulfonyl group, cyclopentyl sulfonyl group, and cyclohexyl sulfonyl group; organic sulfonyl groups in which the sulfur atom directly bonds to an alicyclic ring originating from a bridged alicyclic hydrocarbon such as bicyclo[2.2.1]heptane-2-sulfonyl group, bicyclo [2.2.2]octane-2-sulfonyl group, tetracyclo[4.2.0.$1^{2.5}$.$1^{7.10}$] dodecan-3-sulfonyl group, and adamantane-2-sulfonyl group; organic sulfonyl groups obtainable by bonding of a methylene group or an alkylene group having 2-8 carbon atoms (for example, an ethylene group, a propylene group, etc.) with a cycloalkane such as cyclopropane, cyclobutane, cyclopentane, and cyclohexane or an alicyclic ring originating from a bridged alicyclic hydrocarbon such as norbornane, bicyclo[2.2.2]octane, tricyclodecane, tetracyclododecane, and adamantane (provided that the methylene group or alkylene group bonds to a sulfur atom); and the like can be given. The group $R^1$ in the formula (I) preferably bonds to the 6-position of the naphthalene ring.

As the group $R^1$ in the formula (I), the following groups are preferable: a fluorine atom, methyl group, n-butyl group, n-pentyl group, n-hexyl group, n-heptyl group, n-octyl group, cyclohexyl group, bicyclo[2.2.1]heptan-2-yl group, bicyclo[2.2.2]octan-2-yl group, tetracyclo[4.2.0.$1^{2.5}$.$0^{7.10}$] dodec-3-yl group, (bicyclo[2.2.1]heptan-2-yl)methyl group, (bicyclo[2.2.2]octan-2-yl)methyl group, (tetracyclo [4.2.0.$1^{2.5}$.$1^{7.10}$]dodecan-3-yl)methyl group, methoxy group, n-butoxy group, n-pentyloxy group, n-hexyloxy group, n-heptyloxy group, n-octyloxy group, cyclopentyloxy group, cyclohexyloxy group, (bicyclo[2.2.1]heptan-2-yl)oxy group, (bicyclo[2.2.2]octan-2-yl)oxy group, (tetracyclo[4.2.0.$1^{2.5}$.$1^{7.10}$]dodecan-3-yl)oxy group, cyclopentylmethoxy group, cyclohexylmethoxy group, (bicyclo[2.2.1]heptan-2-yl)methoxy group, (bicyclo[2.2.2]octan-2-yl)methoxy group, (tetracyclo[4.2.0.$1^{2.5}$.$1^{7.10}$]dodecan-3-yl)methoxy group, n-butylsulfanyl group, n-pentylsulfanyl group, n-hexylsulfanyl group, n-heptylsulfanyl group, n-octylsulfanyl group, cyclopentyl sulfanyl group, cyclohexyl sulfanyl group, (bicyclo[2.2.1]heptan-2-yl)sulfanyl group, (bicyclo[2.2.2]octan-2-yl)sulfanyl group, (tetracyclo[4.2.0.$1^{2.5}$.$1^{7.10}$]dodecan-3-yl)sulfanyl group, (bicyclo[2.2.1]heptan-2-yl)methylsulfanyl group, (bicyclo [2.2.2]octan-2-yl)methylsulfanyl group, (tetracyclo [4.2.0.$1^{2.5}$.$1^{7.10}$]dodecan-3-yl)methylsulfanyl group, n-butanesulfonyl group, n-pentanesulfonyl group, n-hexanesulfonyl group, n-heptanesulfonyl group, n-octanesulfonyl group, bicyclo[2.2.1]heptane-2-sulfonyl group, bicyclo[2.2.2]octane-2-sulfonyl group, tetracyclo [4.2.0.$1^{2.5}$.$1^{7.10}$]dodecane-3-sulfonyl group, (bicyclo[2.2.1] heptan-2-yl)methanesulfonyl group, (bicyclo[2.2.2]octan-2-yl)methanesulfonyl group, and (tetracyclo[4.2.0.$1^{2.5}$.$1^{7.10}$] dodecan-3-yl)methanesulfonyl group.

As the linear, branched, or cyclic alkyl group having 1-14 carbon atoms represented by $R^2$ in the formula (I), a methyl group, ethyl group, n-propyl group, i-propyl group, n-butyl group, 2-methylpropyl group, 1-methylpropyl group, t-butyl group, n-pentyl group, n-hexyl group, n-heptyl group, n-octyl group, n-nonyl group, n-decyl group, n-undecyl group, n-dodecyl group, t-dodecyl group, n-tridecyl group, n-tetradecyl group, cyclopropyl group, cyclobutyl group, cyclopentyl group, cyclohexyl group, and the like can be given.

As the substituent for the substituted linear, branched, or cyclic alkyl group having 1-14 carbon atoms represented by $R^2$, one or more groups among a hydroxyl group, carboxyl group, oxo group (=O), cyano group, linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkoxy group having 2-8 carbon atoms (e.g., a methoxymethoxy group, ethoxymethoxy group, t-butoxymethoxy group, etc.), linear or branched alkylcarbonyloxy group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), halogen atom (e.g., a fluorine atom, chlorine atom, etc.), and the like can be given.

The rings of the monocyclic structure having 3-14 carbon atoms or polycyclic structure having 6-14 carbon atoms formed by bonding of two or more $R^2$ groups may be either a carbon ring or a ring containing one or more hetero atoms such as a nitrogen atom, oxygen atom, sulfur atom, etc.

The following can be given as examples of the monocyclic or polycyclic rings: ring structures originating from a cycloalkane such as a cyclopropane, cyclobutane, cyclopentane, and cyclohexane; ring structures originating from a bridged alicyclic hydrocarbon such as norbornane, bicyclo [2.2.2]octane, tricyclodecane, tetracyclododecane, and adamantane; ring structures obtainable by substituting these ring structures with one or more substituents selected from the group consisting of a hydroxyl group, carboxyl group, oxo group (=O), cyano group, halogen atom (e.g., a fluorine atom, a chlorine atom, etc.), linear or branched alkyl group having 1-14 carbon atoms (e.g., a methyl group, ethyl group, n-propyl group, i-propyl group, n-butyl group, 2-methylpropyl group, 1-methylpropyl group, t-butyl group, etc.), linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkyl group having 2-8 carbon atoms (e.g., a methoxymethyl group, ethoxymethyl group, t-butoxymethyl group, etc.), linear or branched alkoxyalkoxy group having 2-8 carbon atoms (e.g., a methoxymethoxy group, ethoxymethoxy group, t-butoxymethoxy group, etc.), linear or branched alkylcarbonyloxy group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), linear or branched cyanoalkyl group having 2-14 carbon atoms (e.g., a cyanomethyl group, 2-cyanoethyl group, 3-cyanopropyl group, 4-cyanobutyl, etc.), linear or branched fluoroalkyl group having 1-14 carbon atoms (e.g., a fluoromethyl group, trifluoromethyl group, pentafluoroethyl group, etc.), and the like can be given.

As $R^2$ in the formula (I), an alkyl group having 1-3 carbon atoms such as a methyl group, ethyl group, n-propyl group, and i-propyl group are preferable. As the structure formed by bonding of two or more $R^2$ groups, a cyclohexane cyclic structure, norbornane cyclic structure, and tetracyclododecane cyclic structure, either substituted or unsubstituted by one or more of a methyl group and a hydroxyl group are preferable. A more preferable $R^2$ group in the formula (I) is an unsubstituted group among the above alkyl groups and a norbornene ring structure formed by bonding of two or more $R^2$ groups. When $R^2$ is the above alkyl group, the alkyl group preferably bonds to the position next to the sulfur atom. In this instance, since base resistance is further improved by the steric hindrance of the alkyl group, storage stability of the positive-tone radiation-sensitive resin composition containing the photoacid generator using the sulfonium salt compound (I) as an essential component can be improved.

In the formula (I), p is preferably 0-3, and particularly preferably 0 or 1; q is preferably 0-2, and particularly preferably 0; and n is preferably 1-3, and particularly preferably 2.

In another aspect of the present invention, a compound in which p is 1, q is 0, n is 2, and $R^1$ is a linear of branched alkoxyl group having 1-14 carbon atoms or —$OR^3$ (wherein $R^3$ is a monovalent hydrocarbon group having an alicyclic skeleton and containing 3-14 carbon atoms) and preferably the alkoxyl group, in the formula (1) is preferable. In this instance, since the sulfonium salt compound (I) is stabilized by electro-donative properties of the alkoxyl group or $OR^3$ group, thereby further improving the heat resistance and base resistance, storage stability of the positive-tone radiation-sensitive resin composition containing the photoacid generator using the sulfonium salt compound (I) as an essential component is improved. In this instance, the alkoxyl group or the $OR^3$ group preferably bonds to the 6-position of the naphthalene ring, whereby the electro-donating effect to the sulfur atom increases due to the resonance structure via the naphthalene ring. This not only results in further improvement of the heat resistance and base resistance, but also increases transparency in a deep-ultraviolet ray region.

The following groups are given as examples of the sulfonic acid anion represented by $X^-$ in the formula (I): linear or branched alkyl sulfonic acid anions such as a methanesulfonic acid anion, ethanesulfonic acid anion, n-propanesulfonic acid anion, n-butanesulfonic acid anion, n-pentanesulfonic acid anion, and n-hexanesulfonic acid anion; alicyclic sulfonic acid anions such as a cyclohexane sulfonic acid anion and d-camphor-10-sulfonic acid anion; aromatic sulfonic acid anions such as benzenesulfonic acid anion, p-toluenesulfonic acid anion, 4-methoxybenzenesulfonic acid anion, 4-n-octylbenzenesulfonic acid anion, 1-naphthalenesulfonic acid anion, 2-naphthalenesulfonic acid, pyrene-2-sulfonic acid anion, 9-anthracenesulfonic acid anion, and 9,10-dimethoxyanthracene-2-sulfonic acid anion; fluorine-substituted benzenesulfonic acid anion such as 4-fluorobenzenesulfonic acid anion, 3-fluorobenzenesulfonic acid anion, 2-fluorobenzenesulfonic acid anion, 2,4-difluorobenzenesulfonic acid, 3,5-difluorobenzenesulfonic acid, 3,4,5-trifluorobenzenesulfonic acid, and perfluorobenzenesulfonic acid; aromatic sulfonic acid anions having an electron-drawing substituent such as a 4-trifluoromethylbenzenesulfonic acid anion, 3-trifluoromethylbenzenesulfonic acid anion, 2-trifluoromethylbenzenesulfonic acid anion, 2,4-bis(trifluoromethyl)benzenesulfonic acid, and 3,5-bis(trifluoromethyl)phenylbenzenesulfonic acid anion; 1,1-difluoroalkyl sulfonic acid anions such as 1,1-difluoroethanesulfonic acid anion, 1,1-difluoro-n-propanesulfonic acid anion, 1,1-difluoro-n-butanesulfonic acid anion, 1,1-difluoro-n-octanesulfonic acid anion, 2-cyclohexyl-1,1-difluoroethanesulfonic acid anion, and 2-(bicyclo[2.2.1]heptan-2-yl)-1,1-difluoroethane sulfonic-acid anion; trifluoromethansulfonic acid anion, a sulfonic acid anion of the following formula (II) (hereinafter referred to as "sulfonic-acid anion (II)"), $$R^4—CF_2CF_2SO_3^- \quad (II)$$

wherein $R^4$ represents a substituted or unsubstituted, linear or branched alkyl group having 1-14 carbon atoms or a substituted or unsubstituted, monovalent hydrocarbon group with 3-14 carbon atoms having an alicyclic ring.

As the unsubstituted linear or branched alkyl group having 1-14 carbon atoms represented by $R^4$ in the formula (II), a methyl group, ethyl group, n-propyl group, i-propyl group, n-butyl group, 2-methylpropyl group, 1-methylpropyl group, t-butyl group, n-pentyl group, n-hexyl group, n-heptyl group, n-octyl group, n-nonyl group, n-decyl group, n-undecyl group, n-dodecyl group, t-dodecyl group, n-tridecyl group, n-tetradecyl group, and the like can be given.

As the unsubstituted monovalent hydrocarbon group having an alicyclic skeleton and containing 3-14 carbon atoms represented by $R^4$, a cycloalkyl group such as a cyclopropyl group, cyclobutyl group, cyclopentyl group, or cyclohexyl group; a group having an alicyclic ring originating from a bridged alicyclic hydrocarbon such as norbornane, bicyclo[2.2.2]octane, tricyclodecane, tetracyclododecane, or adamantane; a group obtainable by bonding of a methylene group or an alkylene group having 2-8 carbon atoms (e.g., an ethylene group, propylene group, etc.) with these cycloalkyl groups or the alicyclic ring (provided that the methylene group or alkylene group bonds with the tetrafluoroethylene group of the formula (II)); and the like can be given.

As the substituent for the substituted linear or branched alkyl group having 1-14 carbon atoms represented by $R^4$, one or more groups among a hydroxyl group, carboxyl group, oxo group (=O), cyano group, halogen atom (e.g., a fluorine atom, chlorine atom, etc.), linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkoxyl group having 2-8 carbon atoms (e.g., a methoxymethoxy group, ethoxymethoxy group, t-butoxymethoxy group, etc.), linear or branched alkylcarbonyloxy group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), and the like can be given. A fluorine atom is preferable among these.

As the substituent for the substituted monovalent hydrocarbon group having an alicyclic structure and containing 3-14 carbon atoms represented by $R^4$, one or more groups among a hydroxyl group, carboxyl group, oxo group (=O), cyano group, halogen atom (e.g., a fluorine atom, chlorine atom, etc.), linear or branched alkyl group having 1-14 carbon atoms (e.g., a methyl group, ethyl group, n-propyl group, i-propyl group, n-butyl group, 2-methylpropyl group, 1-methylpropyl group, t-butyl group, etc.), linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkyl group having 2-8 carbon atoms (e.g., a methoxymethyl group, ethoxymethyl group, t-butoxymethyl group, etc.), linear or branched alkoxyalkoxyl group having 2-8 carbon atoms (e.g., a methoxymethoxy group, ethoxymethoxy group, t-butoxymethoxy group, etc.), linear or branched alkylcarbonyloxyl group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), linear or branched cyanoalkyl group having 2-8 carbon atoms (e.g., a cyanomethyl group, 2-cyanoethyl group, 3-cyanopropyl group, 4-cyanobutyl, etc.), linear or branched alkoxycarbonyloxy group having 2-8 carbon atoms (e.g., a methoxycarbonyloxy group, ethoxycarbonyloxy group, i-propoxycarbonyloxy group, t-butoxycarbonyloxy group, etc.), and the like can be given.

Particularly preferable groups represented by $R^4$ in the formula (II) are a pentafluoro ethyl group, perfluoro-n-hexyl group, bicyclo[2.2.1]heptan-2-yl group, and the like.

Among the above sulfonic acid anions, the sulfonic acid anions (II), particularly, nonafluoro-n-butane sulfonic acid anion, perfluoro-n-octane sulfonic acid anion, 2-(bicyclo[2.2.1]heptan-2-yl)-1,1,2,2-tetrafluoroethane sulfonic acid anion, and the like are preferable.

Specific examples of sulfonium salt compound (I) include: nonafluoro-n-butanesulfonates such as 1-(naphthalen-2-yl)tetrahydrothiophenium nonafluoro-n-butanesulfonate,
1-(6-methylnaphthalen-2-yl)tetrahydrothiophenium nonafluoro-n-butanesulfonate,
1-(6-n-butyl-naphthalen-2-yl)tetrahydrothiophenium nonafluoro-n-butanesulfonate,
1-(6-n-pentylnaphthalen-2-yl)tetrahydrothiophenium nonafluoro-n-butanesulfonate,
1-(6-n-hexylnaphthalen-2-yl)tetrahydrothiophenium nonafluoro-n-butanesulfonate,
1-(6-n-heptylnaphthalen-2-yl)tetrahydrothiophenium nonafluoro-n-butanesulfonate,
1-(6-n-octylnaphthalen-2-yl)tetrahydrothiophenium nonafluoro-n-butanesulfonate,
1-(6-cyclopentylnaphthalen-2-yl)tetrahydrothiophenium nonafluoro-n-butanesulfonate,
1-(6-cyclohexylnaphthalen-2-yl)tetrahydrothiophenium nonafluoro-n-butanesulfonate,
1-[6-(bicyclo[2.2.1]heptan-2-yl)naphthalen-2-yl]tetrahydrothiophenium nonafluoro-n-butanesulfonate,
1-[6-(bicyclo[2.2.2]octan-2-yl)naphthalen-2-yl]tetrahydrothiophenium nonafluoro-n-butanesulfonate,
1-[6-(tetracyclo[4.2.0.$1^{2.5}$.$1^{7.10}$]dodecan-3-yl)naphthalen-2-yl]tetrahydrothiophenium nonafluoro-n-butanesulfonate,
1-[(6-cyclopentylmethyl)naphthalen-2-yl]tetrahydrothiophenium nonafluoro-n-butanesulfonate,
1-[(6-cyclohexylmethyl)naphthalen-2-yl]tetrahydrothiophenium nonafluoro-n-butanesulfonate,
1-[6-{(bicyclo[2.2.1]heptan-2-yl)methyl}naphthalen-2-yl]tetrahydrothiophenium nonafluoro-n-butanesulfonate,
1-[6-{(bicyclo[2.2.2]octan-2-yl)methyl}naphthalen-2-yl]tetrahydrothiophenium nonafluoro-n-butanesulfonate,
1-[6-{(tetracyclo[4.2.0.$1^{2.5}$.$1^{7.10}$]dodecan-3-yl)methyl}naphthalen-2-yl]-tetrahydrothiophenium nonafluoro-n-butanesulfonate,
1-(6-methoxynaphthalen-2-yl)tetrahydrothiophenium nonafluoro-n-butanesulfonate,
1-(6-n-butoxynaphthalen-2-yl)tetrahydrothiophenium nonafluoro-n-butanesulfonate,
1-(6-n-pentyloxynaphthalen-2-yl)tetrahydrothiophenium nonafluoro-n-butanesulfonate,
1-(6-n-hexyloxynaphthalen-2-yl)tetrahydrothiophenium nonafluoro-n-butanesulfonate,
1-(6-n-heptyloxynaphthalen-2-yl)tetrahydrothiophenium nonafluoro-n-butanesulfonate,
1-(6-n-octyloxynaphthalen-2-yl)tetrahydrothiophenium nonafluoro-n-butanesulfonate,
1-(6-cyclopentyloxynaphthalen-2-yl)tetrahydrothiophenium nonafluoro-n-butanesulfonate,
1-(6-cyclohexyloxynaphthalen-2-yl)tetrahydrothiophenium nonafluoro-n-butanesulfonate,
1-[6-(bicyclo[2.2.1]heptan-2-yloxy)naphthalen-2-yl]tetrahydrothiophenium nonafluoro-n-butanesulfonate,
1-[6-(bicyclo[2.2.2]octan-2-yloxy)naphthalen-2-yl]tetrahydrothiophenium nonafluoro-n-butanesulfonate,
1-[6-(tetracyclo[4.2.0.$1^{2.5}$.$1^{7.10}$]dodecan-3-yloxy)naphthalen-2-yl]tetrahydrothiophenium nonafluoro-n-butanesulfonate,
1-(6-cyclopentylmethoxynaphthalen-2-yl)tetrahydrothiophenium nonafluoro-n-butanesulfonate,
1-(6-cyclohexylmethoxynaphthalen-2-yl)tetrahydrothiophenium nonafluoro-n-butanesulfonate,
1-[6-(bicyclo[2.2.1]heptan-2-ylmethoxy)naphthalen-2-yl]tetrahydrothiophenium nonafluoro-n-butanesulfonate,
1-[6-(bicyclo[2.2.2]octan-2-ylmethoxy)naphthalen-2-yl]tetrahydrothiophenium nonafluoro-n-butanesulfonate,
1-[6-(tetracyclo[4.2.0.$1^{2.5}$.$1^{7.10}$]dodecan-3-ylmethoxy)naphthalen-2-yl]-tetrahydrothiophenium nonafluoro-n-butanesulfonate,
1-(6-methylsulfanylnaphthalen-2-yl)tetrahydrothiophenium nonafluoro-n-butanesulfonate,
1-(6-n-butylsulfanylnaphthalen-2-yl)tetrahydrothiophenium nonafluoro-n-butanesulfonate,
1-(6-n-pentylsulfanylnaphthalen-2-yl)tetrahydrothiophenium nonafluoro-n-butanesulfonate,
1-(6-n-hexylsulfanylnaphthalen-2-yl)tetrahydrothiophenium nonafluoro-n-butanesulfonate,
1-(6-n-heptylsulfanylnaphthalen-2-yl)tetrahydrothiophenium nonafluoro-n-butanesulfonate,
1-(6-n-octylsulfanylnaphthalen-2-yl)tetrahydrothiophenium nonafluoro-n-butanesulfonate,
1-(6-cyclopentylsulfanylnaphthalen-2-yl)tetrahydrothiophenium nonafluoro-n-butanesulfonate,
1-(6-cyclohexylsulfanylnaphthalen-2-yl)tetrahydrothiophenium nonafluoro-n-butanesulfonate,
1-[6-{(bicyclo[2.2.1]heptan-2-yl)sulfanyl}naphthalen-2-yl]tetrahydrothiophenium nonafluoro-n-butanesulfonate,
1-[6-{(bicyclo[2.2.2]octan-2-yl)sulfanyl}naphthalen-2-yl]tetrahydrothiophenium nonafluoro-n-butanesulfonate, 1-[6-{(tetracyclo[4.2.0.$1^{2.5}$.$1^{7.10}$]dodecan-3-yl) sulfanyl}naphthalen-2-yl]-tetrahydrothiophenium nonafluoro-n-butanesulfonate, 1-(6-cyclopentylmethoxynaphthalen-2-yl)tetrahydrothiophenium nonafluoro-n-butanesulfonate, 1-(6-cyclohexylmethoxynaphthalen-2-yl)tetrahydrothiophenium nonafluoro-n-butanesulfonate, 1-[6-(bicyclo[2.2.1]heptan-2-ylmethoxy)naphthalen-2-yl] tetrahydrothiophenium nonafluoro-n-butanesulfonate, 1-[6-(bicyclo[2.2.2]octan-2-ylmethoxy)naphthalen-2-yl]tetrahydrothiophenium nonafluoro-n-butanesulfonate, 1-[6-(tetracyclo[4.2.0.$1^{2.5}$.$1^{7.10}$]dodecan-3-ylmethoxy) naphthalen-2-yl]-tetrahydrothiophenium nonafluoro-n-butanesulfonate, 1-(6-methanesulfonylnaphthalen-2-yl)tetrahydrothiophenium nonafluoro-n-butanesulfonate, 1-(6-ethanesulfonylnaphthalen-2-yl)tetrahydrothiophenium nonafluoro-n-butanesulfonate, 1-(6-n-buthanesulfonylnaphthalen-2-yl)tetrahydrothiophenium nonafluoro-n-butanesulfonate, 1-(6-n-pentanesulfonylnaphthalen-2-yl)tetrahydrothiophenium nonafluoro-n-butanesulfonate, 1-(6-n-hexanesulfonylnaphthalen-2-yl)tetrahydrothiophenium nonafluoro-n-butanesulfonate, 1-(6-n-heptanesulfonylnaphthalen-2-yl)tetrahydrothiophenium nonafluoro-n-butanesulfonate, 1-(6-n-octanesulfonylnaphthalen-2-yl)tetrahydrothiophenium nonafluoro-n-butanesulfonate, 1-(6-cyclopentanesulfonylnaphthalen-2-yl)tetrahydrothiophenium nonafluoro-n-butanesulfonate, 1-(6-cyclohexanesulfonylnaphthalen-2-yl)tetrahydrothiophenium nonafluoro-n-butanesulfonate, 1-[6-(bicyclo[2.2.1]heptan-2-sulfonyl)naphthalen-2-yl]tetrahydrothiophenium nonafluoro-n-butanesulfonate, 1-[6-(bicyclo[2.2.2]octan-2-sulfonyl)naphthalen-2-yl]tetrahydrothiophenium nonafluoro-n-butanesulfonate, 1-[6-(tetracyclo[4.2.0.$1^{2.5}$.$1^{7.10}$]dodecan-3-sulfonyl)naphthalen-2-yl]-tetrahydrothiophenium nonafluoro-n-butanesulfonate, 1-[6-(bicyclo[2.2.1]heptan-2-yl)methanesulfonylnaphthalen-2-yl]tetrahydrothiophenium nonafluoro-n-butanesulfonate, 1-[6-(bicyclo[2.2.2]octan-2-yl)methanesulfonylnaphthalen-2-yl]tetrahydrothiophenium nonafluoro-n-butanesulfonate, 1-[6-(tetracyclo[4.2.0.$1^{2.5}$.$1^{7.10}$]dodecan-3-yl)methanesulfonylnaphthalen-2-yl]-tetrahydrothiophenium nonafluoro-n-butanesulfonate, and compounds obtainable by replacing a nonafluoro-n-butanesulfonic acid anion in these nonafluoro-n-butane sulfonates with a perfluoro-n-octanesulfonic acid anion or 2-(bicyclo[2.2.1]heptan-2-yl)-1,1,2,2,-tetrafluoroethanesulfonic acid anion.

Of these sulfonium-salt compounds (I), the following compounds are preferable:

1-(6-methoxynaphthalen-2-yl)tetrahydrothiophenium nonafluoro-n-butanesulfonate, 1-(6-n-butoxynaphthalen-2-yl)tetrahydrothiophenium nonafluoro-n-butanesulfonate, 1-(6-n-pentyloxynaphthalen-2-yl)tetrahydrothiophenium nonafluoro-n-butanesulfonate, 1-(6-n-hexyloxynaphthalen-2-yl)tetrahydrothiophenium nonafluoro-n-butanesulfonate, 1-(6-n-heptyloxynaphthalen-2-yl)tetrahydrothiophenium nonafluoro-n-butanesulfonate, 1-(6-n-octyloxynaphthalen-2-yl)tetrahydrothiophenium nonafluoro-n-butanesulfonate, 1-(6-cyclopentyloxynaphthalen-2-yl)tetrahydrothiophenium nonafluoro-n-butanesulfonate, 1-(6-cyclohexyloxynaphthalen-2-yl)tetrahydrothiophenium nonafluoro-n-butanesulfonate, 1-[6-(bicyclo[2.2.1]heptan-2-yloxy)naphthalen-2-yl]tetrahydrothiophenium nonafluoro-n-butanesulfonate, 1-[6-(bicyclo[2.2.2]octan-2-yloxy)naphthalen-2-yl]tetrahydrothiophenium nonafluoro-n-butanesulfonate, 1-[6-(tetracyclo[4.2.0.$1^{2.5}$.$1^{7.10}$]dodecane-3-yloxy)naphthalen-2-yl]-tetrahydrothiophenium nonafluoro-n-butanesulfonate, 1-(6-cyclopentylmethoxynaphthalen-2-yl)tetrahydrothiophenium nonafluoro-n-butanesulfonate, 1-(6-cyclohexylmethoxynaphthalen-2-yl)tetrahydrothiophenium nonafluoro-n-butanesulfonate, 1-[6-(bicyclo[2.2.1]heptan-2-ylmethoxy)naphthalen-2-yl] tetrahydrothiophenium nonafluoro-n-butanesulfonate, 1-[6-(bicyclo[2.2.2]octan-2-ylmethoxy)naphthalen-2-yl]tetrahydrothiophenium nonafluoro-n-butanesulfonate, 1-[6-(tetracyclo[4.2.0.$1^{2.5}$.$1^{7.10}$]dodecan-3-ylmethoxy) naphthalen-2-yl]-tetrahydrothiophenium nonafluoro-n-butanesulfonate, and compounds obtainable by replacing a nonafluoro-n-butanesulfonic acid anion in these nonafluoro-n-butane sulfonates with a perfluoro-n-octanesulfonic acid anion or 2-(bicyclo[2.2.1]heptan-2-yl)-1,1,2,2,-tetrafluoroethanesulfonic acid anion.

The onium salt compound (I) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a radiation-sensitive resin composition useful as a chemically amplified photoresist in the field of microfabrication represented by the manufacture of semiconductor devices, but is also useful as a raw material for the synthesis of a heat acid generator which generates an acid with heating and other related onium salt compounds.

Synthesis of Sulfonium Salt Compound (I)

The sulfonium compound (I) can be manufactured by, for example, a process shown by the following reaction formula (a) or (b), wherein n and $X^-$ are respectively the same as the n and $X^-$ in the formula (I), X represents an atom or atomic group providing $X^-$, and Z is a dissociable substituent such as a halogen and a sulfonate. In the formulas, substituents $R^1$ and $R^2$ are omitted.

Reaction formula (a)

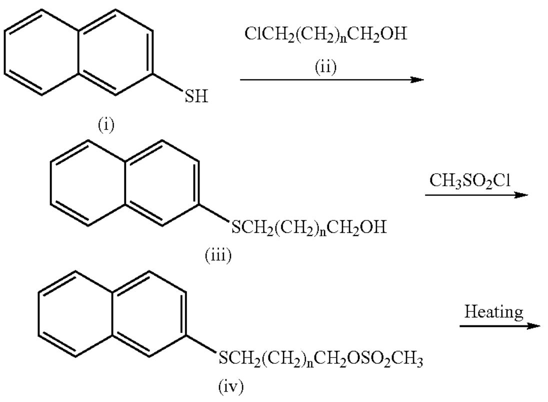

(i)

(iii)

(iv)

-continued

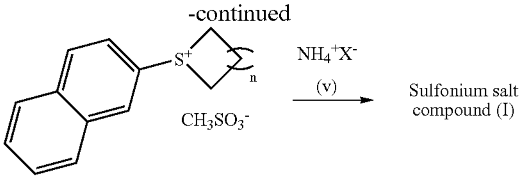

Reaction formula (b)

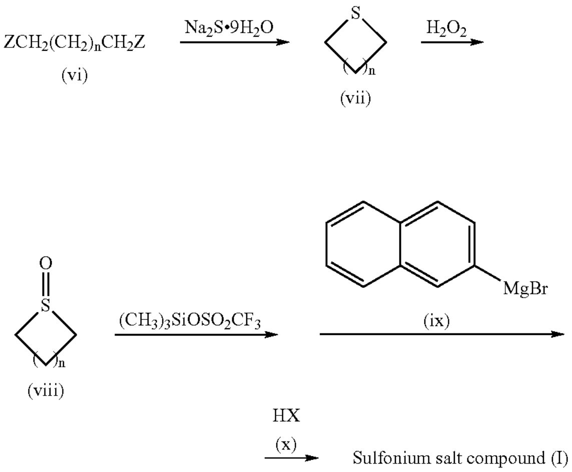

In the reaction formula (a), 2-naphthalene thiol (i) is reacted with α-chloro-ω-alkanol (ii) in the presence of an organic base such as triethylamine to obtain 2-(ω-hydroxy-alkyl sulfanyl)naphthalene (iii). The 2-(ω-hydroxyalkyl sulfanyl)naphthalene (iii) is then reacted with methanesulfonyl chloride in the presence of an organic base to obtain a methansulfonic acid ester (iv). The methansulfonic acid ester (iv) is then cyclized with heating and converted into a sulfonium methane sulfonate salt, which is reacted with an ammonium salt or an alkali metal salt of $X^-$ for ion-exchange, thereby obtaining the sulfonium-salt compound (I).

The 2-naphthalene thiol used in the reaction formula (a) can be prepared using, for example, a method of transforming 2-naphthalene sulfonic acid into sulfonyl chloride using a chlorinating agent and reducing the sulfonyl chloride (see J. Org. Chem., Vol. 57, p. 2631-2641(1992), Liebigs Ann. Chem., p. 1112-1140(1973)), a method of directly reducing 2-naphthalene sulfonic acid (see Bull. Chem. Soc. Jpn., p. 3802-3812 (1983)), a method of using a nucleophilic substitution reaction of 2-naphthyl diazonium salt and a sulfur anion (see J. Prakt. Chim., Vol. 41, p. 218 (1890)), a method of transforming a 2-halogenated naphthalene into a corresponding organolithium compound or a corresponding Grignard reagent and reacting with sulfur (see Bull. Soc. Chim. Belg., Vol. 65, p. 874-891 (1956)), and a method of reacting 2-bromonaphthalene with a low-alkyl thiorate (see Synthesis, p. 751-755 (1983)).

In the reaction formula (b), a cyclic thioether (vii) obtained by the nucleophilic substitution reaction of α,ω-disubstituted alkane (vi) and sodium sulfide is oxidized with an equivalent amount of hydrogen peroxide in the presence of a catalytic amount of sodium tungstate at 0° C. to obtain a cyclic sulfoxide (viii). After reacting the cyclic sulfoxide (viii) with trimethylsilyl trifluoromethane sulfonate at a low temperature of about −78° C. according to the method described in J. Org. Chem., Vol. 43, p. 5571-5573 (1988), for example, the reaction product is reacted with a Grignard reagent (ix), then with an acid (x) to obtain the sulfonium salt compound (I).

Each reaction is usually carried out in an appropriate solvent.

As the solvent, an appropriate solvent is selected from among water, methanol, ethanol, acetone, dichloromethane, tetrahydrofuran, acetonitrile, 1-methylpyrrolidone, N,N-dimethylformamide, a dichloromethane-tetrahydrofuran mixed solvent, diethyl ether, benzene, toluene, a diethyl-ether-toluene mixed solvent, a diethyl-ether-benzene mixed solvent, and the like.

Photoacid Generator

The photoacid generator of the present invention, which is an sulfonium salt compound (I), generates an acid when exposed to radiation, and is suitably used as a photoacid generator for a radiation-sensitive resin composition useful for microfabrication utilizing various types of radiation represented by deep ultraviolet rays such as a KrF excimer laser, ArF excimer laser, $F_2$ excimer laser, and EUV, and electron beams. Hereinafter, the photoacid generators of the sulfonium salt compound (I) will be referred to as "acid generator (A1)".

Positive-tone Radiation-sensitive Resin Composition

Acid Generator (A)

The component (A) of the positive-tone radiation-sensitive resin composition of the present invention is a photoacid generator (hereinafter referred to as "acid generator (A)") comprising the photoacid generator (A1) as an essential component.

The acid generator (A1) can be used either individually or in combination of two or more in the positive-tone radiation sensitive resin composition of the present invention.

One or more photoacid generators other than the acid generator (A1) (hereinafter referred to as "other acid generators") can be used in combinations in the positive-tone radiation-sensitive resin composition of the present invention.

As examples of the other acid generators, onium salt compounds, sulfone compounds, sulfonate compounds, sulfonimide compounds, diazomethane compounds, disulfonylmethane compounds, oximesulfonate compound, and the like can be given.

As examples of onium salt compounds, iodonium salts, sulfonium salts (including tetrahydrothiophenium salts), phosphonium salts, diazonium salts, ammonium salts, pyridinium salts, and the like can be given.

As examples of the sulfone compound, β-ketosulfone, β-sulfonylsulfone, and α-diazo compounds of these compounds can be given.

As examples of the sulfonate compound, alkyl sulfonate, haloalkyl sulfonate, aryl sulfonate, and imino sulfonate can be given.

As an example of the sulfonimide compound, a compound of the following formula (1), and the like can be given:

(1)

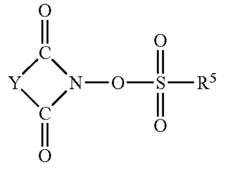

wherein Y is a divalent organic group and $R^5$ is a monovalent organic group.

As examples of Y in the formula (1), a methylene group, linear or branched alkylene group having 2-20 carbon atoms, aralkylene group having 2-20 carbon atoms, difluoromethylene group, linear or branched perfluoroalkylene group having 2-20 carbon atoms, cyclohexylene group, phenylene group, substituted or unsubstituted divalent group possessing a norbornene skeleton, or a group wherein these groups are substituted with an aryl group having six or more carbon atoms or an alkoxyl group having one or more carbon atoms can be given.

As examples of $R^5$, a linear or branched alkyl group having 1-10 carbon atoms, linear or branched perfluoroalkyl group having 1-10 carbon atoms, perfluorocycloalkyl group having 3-10 carbon atoms, monovalent hydrocarbon group possessing a bicyclo ring having 7-15 carbon atoms, and an aryl group having 6-12 carbon atoms, can be given.

As an example of the diazomethane compound, a compound of the following formula (2), and the like can be given:

(2)

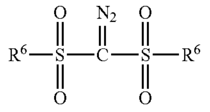

wherein $R^6$ individually represents a monovalent group such as a linear or branched alkyl group, cycloalkyl group, aryl group, halogenated alkyl group, halogenated cycloalkyl group, and halogenated aryl group.

As an example of the disulfonylmethane compound, a compound of the following formula (3) can be given:

(3)

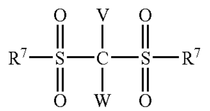

wherein $R^7$ individually represents a linear or branched monovalent aliphatic hydrocarbon group, cycloalkyl group, aryl group, aralkyl group, other monovalent organic group having a hetero atom, V and W individually represent an aryl group, hydrogen atom, a linear or branched monovalent aliphatic hydrocarbon group, a cycloalkyl group, aralkyl group, or other monovalent organic group having a hetero atom, provided that at least one of V and W represents an aryl group, or V and W bond to form a monocyclic or polycyclic ring having at least one unsaturated bond, or V and W bond to form a group shown by the following formula (4);

(4)

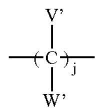

wherein V's and W's individually represent a hydrogen atom, halogen atom, linear or branched alkyl group, cycloalkyl group, aryl group, or aralkyl group, or V' and W', each bonded to the same or different carbon atoms, may form a monocarbocyclic structure, and j is an integer from 2 to 10.

As examples of the oxime sulfonate compound, compounds of the following formula (5-1) or (5-2) can be given:

(5-1)

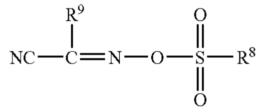

(5-2)

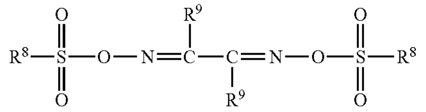

wherein $R^8$ and $R^9$ individually represent a monovalent organic group.

As specific examples of $R^8$ in the formulas (5-1) and (5-2), a methyl group, ethyl group, n-propyl group, phenyl group, and tosyl group can be given. As specific examples of $R^9$, a phenyl group, tosyl group, 1-naphthyl group, trifluoromethyl group, and nonafluoro-n-butyl group can be given.

At least one acid generator selected from the group consisting of an onium salt compound, sulfonimide compound, and diazomethane compound is preferably used as the other acid generator.

As specific preferable examples of the other acid generator, at least one compounds selected from the group consisting of:

bis(4-t-butylphenyl)iodonium trifluoromethane sulfonate,
bis(4-t-butylphenyl)iodonium nonafluoro-n-butanesulfonate,
bis(4-t-butylphenyl)iodonium p-toluenesulfonate,
bis(4-t-butylphenyl)iodonium 10-camphorsulfonate,
bis(4-t-butylphenyl)iodonium 2-trifluoromethylbenzenesulfonate,
bis(4-t-butylphenyl)iodonium 4-trifluoromethylbenzenesulfonate,
bis(4-t-butylphenyl)iodonium 2,4-difluorobenzenesulfonate,
triphenylsulfonium trifluoromethanesulfonate,
triphenylsulfonium nonafluoro-n-butanesulfonate,
triphenylsulfonium p-toluenesulfonate,
triphenylsulfonium 10-camphorsulfonate,
triphenylsulfonium 2-trifluoromethylbenzenesulfonate,
triphenylsulfonium 4-trifluorobenzenesulfonate,
triphenylsulfonium 2,4-difluorobenzenesulfonate,
4-fluorophenyl.diphenylsulfonium nonafluoro-n-butanesulfonate,
4-methoxyphenyl.diphenylsulfonium nonafluoro-n-butanesulfonate, 4-n-butanesulfonyloxyphenyl.diphenylsulfonium nonafluoro-n-butanesulfonate, 4-cyclohexylphenyl.diphenylsulfonium nonafluoro-n-butanesulfonate, 4-t-butylphenyl.diphenylsulfonium nonafluoro-n-butanesulfonate, 4-n-butanesulfonylphenyl.diphenylnonafluoro-n-butanesulfonate, 4-cyclohexanesulfonylphenyl.diphenylsulfonium nonafluoro-n-butanesulfonate, 2-methylphenyl.diphenylnonafluoro-n-butanesulfonate, 2,4-dimethylphenyl.diphenylnonafluorobutanesulfonate, mesityl.diphenylsulfonium nonafluoro-n-butanesulfonate, 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, compounds of the formulas (6-1) to (6-8) (wherein n-$C_4F_9SO_3^-$ is a nonafluoro-n-butanesulfonate anion), (6-1)

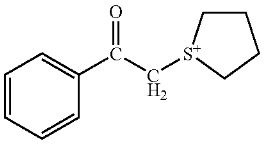

n-$C_4H_9SO_3^-$ (6-2)

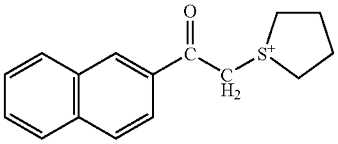

n-$C_4H_9SO_3^-$ (6-3)

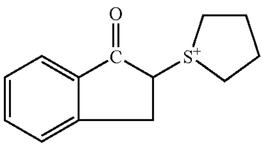

n-$C_4H_9SO_3^-$ (6-4)

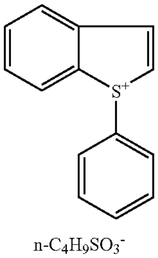

n-$C_4H_9SO_3^-$ (6-5)

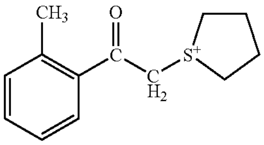

n-$C_4H_9SO_3^-$

-continued (6-6)

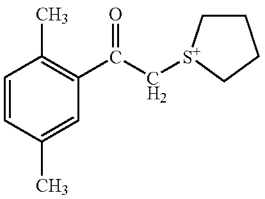

n-$C_4H_9SO_3^-$ (6-7)

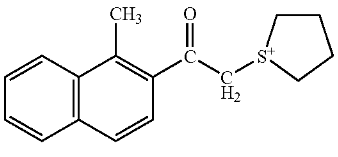

n-$C_4H_9SO_3^-$ (6-8)

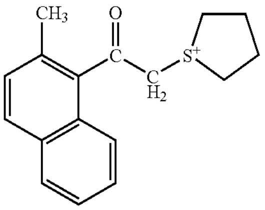

n-$C_4H_9SO_3^-$

N-(trifluoromethanesulfonyloxy)succinimide,
N-(trifluoromethanesulfonyloxy)bicyclo[2.2.1]hept-5-ene-2,3-dicarboxyimide,
N-(10-camphorsulfonyloxy)succinimide,
N-(10-camphorsulfonyloxy)bicyclo[2.2.1]hept-5-ene-2,3-dicarboxyimide,
N-[(5-methyl-5-carboxymethylbicyclo[2.2.1]hept-2-yl)sulfonyloxy]succinimide,
bis(cyclohexanesulfonyl)diazomethane,
bis(t-butylsulfonyl)diazomethane, and
bis(1,4-dioxaspiro[4.5]-decane-7-sulfonyl)diazomethane can be given.

The proportion of other acid generators can be appropriately determined depending on the types of each acid generator. The proportion is 95 parts by weight or less, preferably 90 parts by weight or less, and particularly preferably 80 parts by weight or less for 100 parts by weight of the total amount of the acid generator (A1) and the other acid generators. If the proportion of the other acid generators exceeds 95 parts by weight, the desired effects of the present invention may be impaired.

(B) Acid-dissociable Group-containing Resin

The component (B) of the positive-tone radiation sensitive resin composition of the present invention is an acid-dissociable group-containing resin which is insoluble or scarcely soluble in alkali, but becomes easily soluble in alkali when the acid-dissociable group dissociates (hereinafter referred to as "acid-dissociable group-containing resin (B)").

If 50% or more of the initial film thickness of a resist film remains after development when the resist film made only from the acid-dissociable group-containing resin (B) is developed under the same alkaline development conditions employed for forming a resist pattern using a resist film formed from a radiation-sensitive resin composition comprising the acid-dissociable group-containing resin (B), such a characteristic of the acid-dissociable group-containing resin (B) is referred to as "insoluble or scarcely soluble in alkali" in the present invention.

The acid-dissociable group of the acid-dissociable group-containing resin (B) refers to a group which is replaced with the hydrogen atom in an acid-functional group such as a phenolic hydroxyl group, carboxyl group, and sulfonic group and is dissociable in the presence of an acid.

As examples of such an acid-dissociable group, a t-butoxycarbonyl group, tetrahydropyranyl group, tetrahydrofuranyl group, (thiotetrahydropyranylsulfanyl)methyl group, (thiotetrahydrofuranylsulfanyl)methyl group, alkoxy-substituted methyl group, alkylsulfanyl-substituted methyl group, a group represented by the following general formula (7) (hereinafter referred to as "acid-dissociable group (7)"), and the like can be given.

(7)

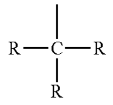

wherein R individually represents a linear or branched alkyl group having 1-14 carbon atoms or a bridged or unbridged monovalent alicyclic hydrocarbon group having 3-20 carbon atoms, or any two of R groups bond to form a bridged or unbridged divalent alicyclic hydrocarbon group having 3-20 carbon atoms, with the remaining R being a linear or branched alkyl group having 1-14 carbon atoms or a bridged or unbridged monovalent alicyclic hydrocarbon group having 3-20 carbon atoms, wherein all these groups are either substituted or unsubstituted.

As examples of the alkoxy-substituted methyl group, a methoxymethyl group, ethoxymethyl group, methoxyethoxymethyl group, n-propoxymethyl group, n-butoxymethyl group, n-pentyloxymethyl group, n-hexyloxymethyl group, benzyloxymethyl group, and the like can be given.

As examples of the alkylsulfanyl-substituted methyl group, a methylsulfanylmethyl group, ethylsulfanylmethyl group, methoxyethylsulfanylmethyl group, n-propylsulfanylmethyl group, n-butylsulfanylmethyl group, n-pentylsulfanylmethyl group, n-hexylsulfanylmethyl group, benzylsulfanylmethyl group, and the like can be given.

In the formula (7), as examples of the linear or branched alkyl group having 1-14 carbon atoms represented by R, a methyl group, ethyl group, n-propyl group, i-propyl group, n-butyl group, 2-methylpropyl group, n-pentyl group, n-hexyl group, n-heptyl group, n-octyl group, n-nonyl group, n-decyl group, n-undecyl group, n-dodecyl group, n-tridecyl group, n-tetradecyl group, and the like can be given.

As the substituent for the alkyl group, one or more groups among a hydroxyl group, carboxyl group, oxo group (═O), cyano group, halogen atom (e.g., a fluorine atom, chlorine atom, etc.), linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkoxy group having 2-8 carbon atoms (e.g., a methoxymethoxy group, ethoxymethoxy group, t-butoxymethoxy group, etc.), linear or branched alkylcarbonyloxy group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), and the like can be given.

As examples of the bridged or unbridged monovalent alicyclic hydrocarbon group having 3-20 carbon atoms represented by R, cycloalkyl groups such as a cyclopropyl group, cyclobutyl group, cyclopentyl group, cyclohexyl group, cycloheptyl group, and cyclooctyl group; a bicyclo [2.2.1]heptyl group, bicyclo[2.2.2]octyl group, tetracyclo $[4.2.0.1^{2,5}.1^{7,10}]$dodecyl group, adamantyl group, and the like can be given.

As the substituent for the above monovalent alicyclic hydrocarbon group represented by R or the substituent for the above divalent alicyclic hydrocarbon group formed by bonding of any two R groups, one or more groups among a hydroxyl group, carboxyl group, oxo group (═O), cyano group, halogen atom (e.g., a fluorine atom, chlorine atom, etc.), linear or branched alkyl group having 1-14 carbon atoms (e.g., a methyl group, ethyl group, n-propyl group, i-propyl group, n-butyl group, 2-methylpropyl group, 1-methylpropyl group, t-butyl group, etc.), linear or branched alkoxyl group having 1-8 carbon atoms (e.g., a methoxy group, ethoxy group, n-propoxy group, i-propoxy group, n-butoxy group, 2-methylpropoxy group, 1-methylpropoxy group, t-butoxy group, etc.), linear or branched alkoxyalkyl group having 2-8 carbon atoms (e.g., a methoxymethyl group, ethoxymethyl group, t-butoxymethyl group, etc.), linear or branched alkoxyalkoxy group having 2-8 carbon atoms (e.g., a methoxymethoxy group, ethoxymethoxy group, t-butoxymethoxy group, etc.), linear or branched alkylcarbonyloxy group having 2-8 carbon atoms (e.g., a methylcarbonyloxy group, ethylcarbonyloxy group, t-butylcarbonyloxy group, etc.), linear or branched alkoxycarbonyl group having 2-8 carbon atoms (e.g., a methoxycarbonyl group, ethoxycarbonyl group, t-butoxycarbonyl group, etc.), linear or branched cyanoalkyl group having 2-14 carbon atoms (e.g., a cyanomethyl group, 2-cyanoethyl group, 3-cyanopropyl group, 4-cyanobutyl, etc.), linear or branched fluoroalkyl group having 1-14 carbon atoms (e.g., a fluoro methyl group, trifluoromethyl group, pentafluoroethyl group, etc.), and the like can be given.

As specific preferable examples of the acid-dissociable group (7), a t-butyl group and groups shown by the following formulas (7-1) to (7-20) (provided that m is an integer of 0-2) can be given.

(7-1)

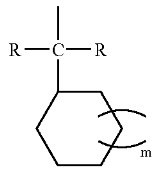

(7-2)

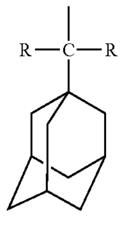

-continued
(7-3)
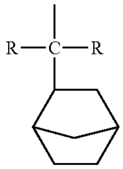
(7-4)
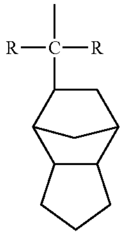
(7-5)
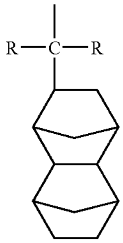
(7-6)
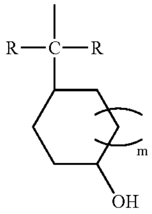
(7-7)
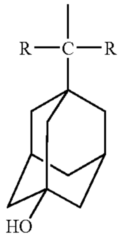
(7-8)
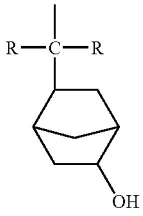
(7-9)
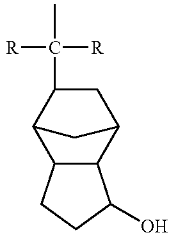
-continued
(7-10)
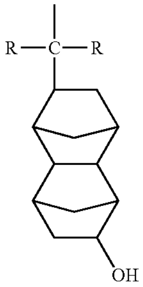
(7-11)
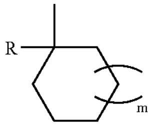
(7-12)
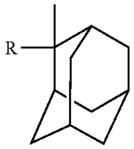
(7-13)
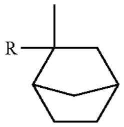
(7-14)
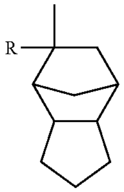
(7-15)
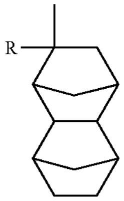
(7-16)
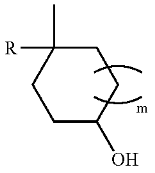
(7-17)
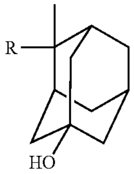

-continued (7-18)

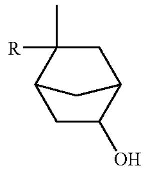

(7-19)

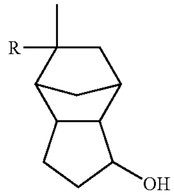

(7-20)

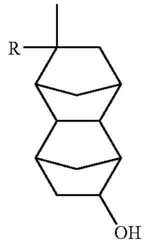

The acid-dissociable group-containing resin (B) may contain one or more acid-dissociable groups.

The amount of the acid-dissociable group introduced into the acid-dissociable group-containing resin (B) (the amount of the number of acid-dissociable groups in the total number of acidic functional groups and acid-dissociable groups in the acid-dissociable group-containing resin (B)) is preferably 5-100%, and still more preferably 10-100%, although the amount varies depending on the type of acid-dissociable group and the type of resin into which the acid-dissociable group is introduced.

Various types of structure for the acid-dissociable group-containing resin (B) may be used without any restrictions as long as the above properties can be obtained. Preferable structures include a poly(p-hydroxystyrene) in which part or all of the hydrogen atoms in the phenolic hydroxyl groups are replaced by acid-dissociable groups, a copolymer of p-hydroxystyrene and/or p-hydroxy-α-methylstyrene and (meth)acrylic acid in which part or all of the hydrogen atoms in the phenolic hydroxyl groups and/or carboxyl groups are replaced by acid-dissociable groups, and the like.

Also, the structure of the acid-dissociable group-containing resin (B) can be appropriately determined according to the type of radiation employed. As an acid-dissociable group-containing resin (B) particularly preferable for a radiation-sensitive resin composition using a KrF excimer laser, an alkali-insoluble or scarcely alkali-soluble resin having a recurring unit of the following formula (8) (hereinafter referred to as "recurring unit (8)") and a recurring unit in which the phenolic hydroxyl group in the recurring unit (8) is protected by an acid-dissociable group can be given. This resin is hereinafter referred to as "resin (B1)". The resin (B1) may be suitably used in radiation-sensitive resin compositions for use with other radiations such as ArF excimer laser, $F_2$ excimer laser, and electron beams.

(8)

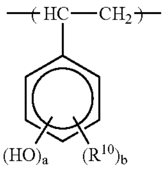

wherein $R^{10}$ individually represent a hydrogen atom or monovalent organic group, two or more $R^{10}$s, if present, may be the same or different, and a and b each represent an integer of 1-3.

As the recurring unit (8), units wherein the non-aromatic double bond of p-hydroxystyrene is cleaved are preferable.

The resin (B1) may further contain other recurring units.

As examples of the other recurring unit, units obtained by cleavage of a polymerizable unsaturated bond of vinyl aromatic compounds such as styrene; (meth)acrylic esters such as t-butyl (meth)acrylate, adamantyl (meth)acrylate, and 2-methyladamantyl (meth)acrylate; and the like can be given.

As the acid-dissociable group-containing resin (B) particularly preferable for a radiation-sensitive resin composition using an ArF excimer laser, an alkali-insoluble or scarcely alkali-soluble resin having a recurring unit of the following formula (9) (hereinafter referred to as "recurring unit (9)") and/or a recurring unit of the following formula (10) (hereinafter referred to as "recurring unit (10)") can be given. This resin is hereinafter referred to as "resin (B2)". The resin (B2) may be suitably used in radiation-sensitive resin compositions for use with other radiations such as KrF excimer laser, $F_2$ excimer laser, and electron beams.

(9)

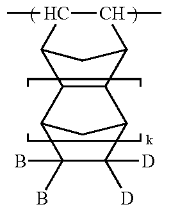

wherein B individually represent a hydrogen atom or a monovalent acid-dissociable group, at least one of B being a monovalent acid-dissociable group, D individually represents a hydrogen atom or a linear or branched alkyl group having 1-4 carbon atoms, and k is an integer of 0-2, or (10)

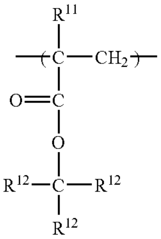

wherein $R^{11}$ represents a hydrogen atom or methyl group and $R^{12}$ individually represents a linear or branched alkyl group having 1-4 carbon atoms or a substituted or unsubstituted monovalent alicyclic hydrocarbon group having 3-20 carbon atoms, or any two of $R^{12}$ groups bond to form a substituted or unsubstituted, bridged or unbridged, divalent alicyclic hydrocarbon group having 3-20 carbon atoms, with the remaining $R^{12}$ group being a linear or branched alkyl group having 1-4 carbon atoms or a substituted or unsubstituted monovalent alicyclic hydrocarbon group having 3-20 carbon atoms.

As preferable examples of the recurring unit (10), a unit originating from t-butyl (meth)acrylate and recurring units shown by the following formulas (10-1) to (10-18) can be given.

(10-1)

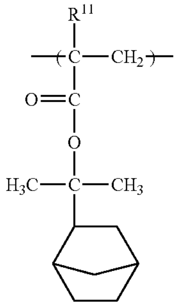

(10-2)

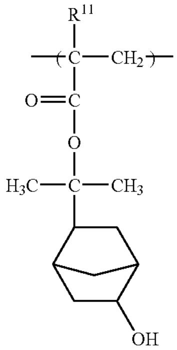

(10-3)

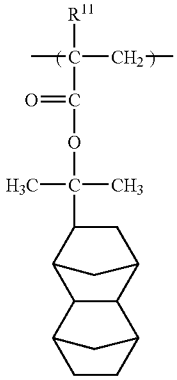

-continued (10-4)

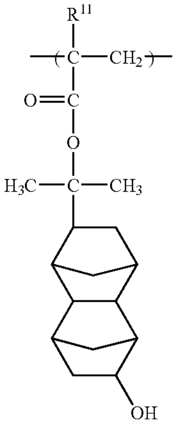

(10-5)

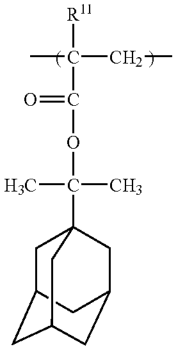

(10-6)

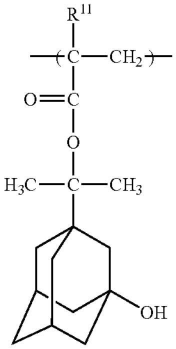

(10-7)

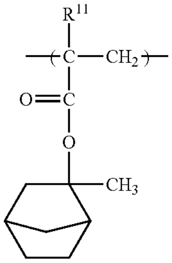

-continued
(10-8)
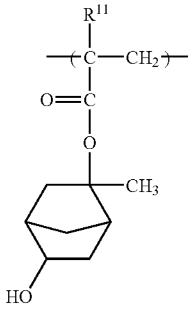
(10-9)
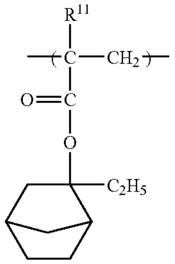
(10-10)
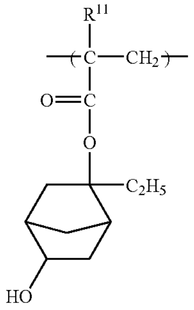
(10-11)
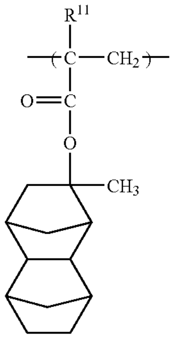
(10-12)
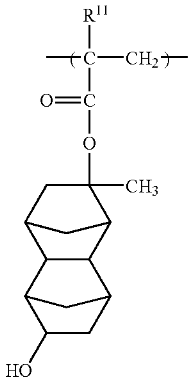
-continued
(10-13)
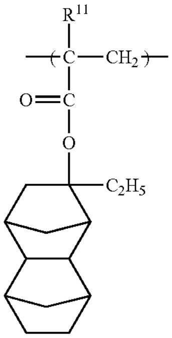
(10-14)
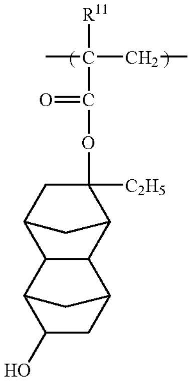
(10-15)
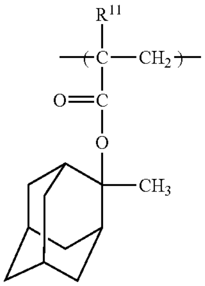
(10-16)
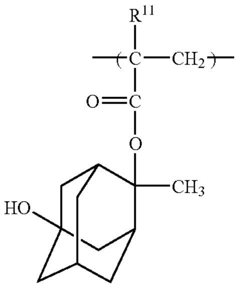
(10-17)
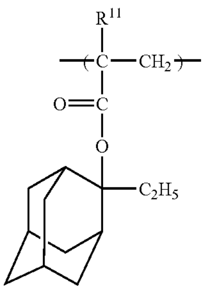

-continued (10-18)

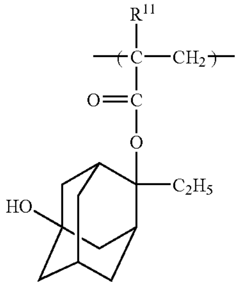

The resin (B2) may further contain one or more types of other recurring units.

As the other recurring units, units obtainable by cleavage of a polymerizable unsaturated bond of monomers having a norbornene skeleton such as, for example, norbornene(bicyclo[2.2.1]hept-2-ene), 5-methylbicyclo[2.2.1]hept-2-ene, 5-ethylbicyclo[2.2.1]hept-2-ene, 5-hydroxybicyclo[2.2.1]hept-2-ene, 5-fluorobicyclo[2.2.1]hept-2-ene, tetracyclo$[4.4.0.1^{2.5}.1^{7.10}]$dodec-3-ene, 8-methyltetracyclo$[4.4.0.1^{2.5}.1^{7.10}]$dodec-3-ene, 8-ethyltetracyclo$[4.4.0.1^{2.5}.1^{7.10}]$dodec-3-ene, 8-hydroxytetracyclo$[4.4.0.1^{2.5}.1^{7.10}]$dodec-3-ene, and 8-fluorotetracyclo$[4.4.0.1^{2.5}.1^{7.10}]$dodec-3-ene; units obtainable by cleavage of a polymerizable unsaturated bond of unsaturated carboxylic anhydride such as maleic anhydride and itaconic anhydride; and units obtainable by cleavage of a polymerizable unsaturated bond of(meth)acrylates of the following formulas (11-1) to (11-8) (hereinafter referred to as "recurring unit (11)") can be given:

(11-1)

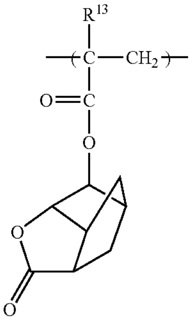

(11-2)

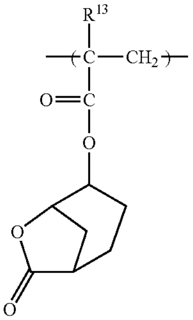

-continued (11-3)

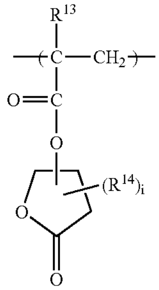

(11-4)

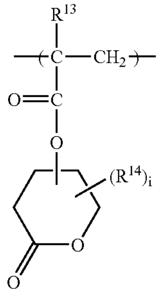

(11-5)

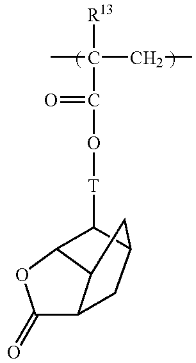

(11-6)

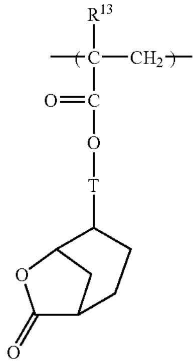

-continued (11-7)

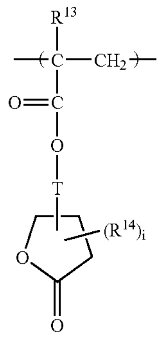

(11-8)

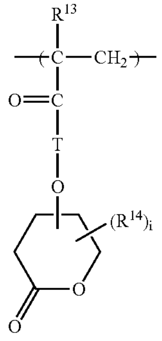

wherein $R^{13}$ individually represents a hydrogen atom or a methyl group, $R^{14}$ individually represents a substituted or unsubstituted alkyl group having 1-14 carbon atoms, a hydroxyl group, or a cyano group, i is an integer of 0-3, and T is a methylene group or an alkylene group having 2-8 carbon atoms.

The resin (B2) having the recurring unit (9) preferably further contains a recurring unit originating from maleic anhydride as the other recurring unit.

The resin (B2) which comprises the recurring unit (10) and the recurring unit (11) preferably further contains at least one recurring unit of the following formulas (12-1) to (12-4) as the other recurring unit.

(12-1)

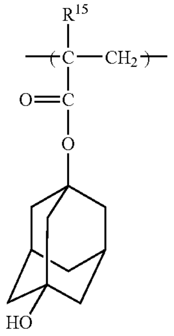

-continued (12-2)

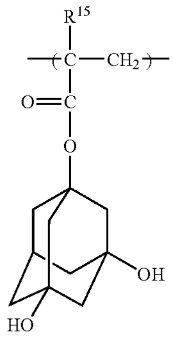

(12-3)

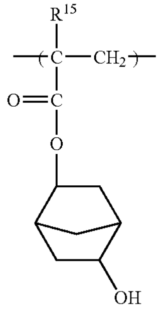

(12-4)

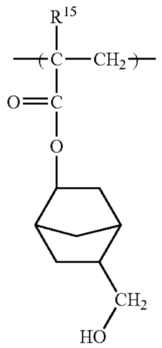

wherein $R^{15}$ individually represents a hydrogen atom or a methyl group,

As the acid-dissociable group-containing resin (B) particularly preferable for a radiation-sensitive resin composition using an $F_2$ excimer laser, an alkali-insoluble or scarcely alkali-soluble polysiloxane having a recurring unit of the following formula (13) (hereinafter referred to as "recurring unit (13)") and/or a recurring unit of the following formula (14) can be given. This resin is hereinafter referred to as "resin (B3)". The resin (B3) may be suitably used in radiation-sensitive resin compositions for use with other radiations such as KrF excimer laser, ArF excimer laser, and electron beams.

(13)

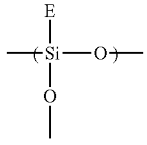

-continued (14)

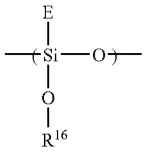

wherein E individually represents a monovalent organic group having an acid-dissociable group and $R^{16}$ represents a substituted or unsubstituted, linear, branched, or cyclic monovalent hydrocarbon group having 1-20 carbon atoms.

E in the formulas (13) and (14) is preferably a group having a structure in which the acid-dissociable group is bonded with a group having a ring skeleton.

As the group having a ring skeleton, a group having an alicyclic structure originating from a cycloalkane having 3-8 carbon atoms, tricyclodecane, tetracyclodecane, adamantane, and the like, and a group having a halogenated aromatic ring skeleton having 6-14 carbon atoms are preferable.

As the resin (B3), a resin having the recurring unit (13) is particularly preferable.

As specific examples of the recurring unit (13), the recurring units of the following formulas (13-1)-(13-4) can be given.

(13-1)

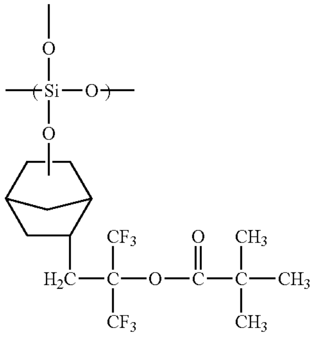

(13-2)

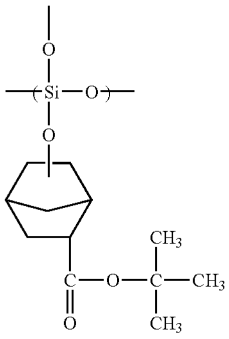

-continued (13-3)

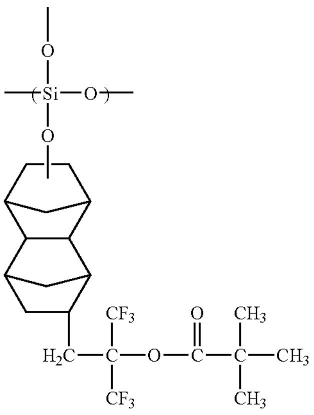

(13-4)

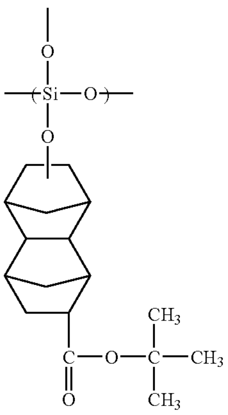

The resin (B3) may further contain one or more types of other recurring units.

As preferable examples of the other recurring units, units obtained from hydrolysis of alkyl alkoxysilanes such as methyl trimethoxysilane, methyl triethoxysilane, ethyl trimethoxysilane, and ethyl triethoxysilane, and the recurring units of the following formulas (15-1)-(15-4) can be given.

(15-1)

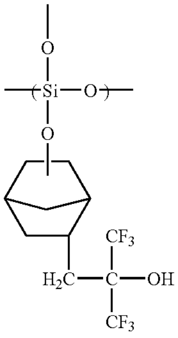

-continued (15-2)

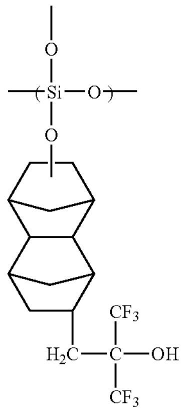

(15-3)

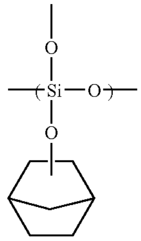

(15-4)

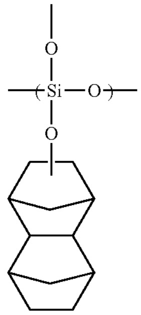

The resin (B3) can be prepared by polycondensation of a silane compound containing an acid-dissociable group or by introducing an acid-dissociable group into a previously prepared polysiloxane.

When polymerizing the acid-dissociable group-containing silane compound, an acidic catalyst is preferably used as the catalyst, and after polycondensation of the silane compound in the presence of the acidic catalyst, a further reaction is preferably continued in the presence of a basic catalyst.

As examples of the acidic catalyst, inorganic acids such as hydrochloric acid, sulfuric acid, nitric acid, boric acid, phosphoric acid, titanium tetrachloride, zinc chloride, and aluminium chloride and organic acids such as formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid can be given.

Of these acidic catalysts, hydrochloric acid, sulfuric acid, acetic acid, oxalic acid, malonic acid, maleic acid, fumaric acid, acetic anhydride, maleic anhydride, and the like are preferable.

These acidic catalysts may be used either individually or in combination of two or more.

As examples of the basic catalyst, inorganic bases such as lithium hydroxide, sodium hydroxide, potassium hydroxide, calcium hydroxide, barium hydroxide, sodium hydrogencarbonate, potassium hydrogencarbonate, sodium carbonate, and potassium carbonate and organic bases such as triethylamine, tri-n-propylamine, tri-n-butylamine, and pyridine can be given.

These basic catalysts may be used either individually or in combination of two or more.

When the acid-dissociable group-containing resin (B) is prepared by a reaction or reactions comprising the polymerization of a polymerizable unsaturated monomer, a branched structure may be introduced into the acid-dissociable group-containing resin by a unit derived from a polyfunctional monomer having two or more polymerizable unsaturated bonds and/or by an acetal crosslinking group. Introduction of the branched structure improves the heat resistance of the acid-dissociable group-containing resin (B).

The amount of the branched structure introduced into the acid-dissociable group-containing resin (B) is preferably 10 mol % or less of the total amount of recurring units, although such an amount varies depending on the type of branched structure and the type of acid-dissociable group-containing resin into which the branched structure is introduced.

The molecular weight of the acid-dissociable group-containing resin (B) may be appropriately selected without any restrictions. The polystyrene-reduced weight molecular weight (hereinafter referred to as "Mw") of the acid-dissociable group-containing resin (B) determined by gel permeation chromatography (GPC) is usually 1,000-500,000, preferably 2,000-400,000, and still more preferably 3,000-300,000.

The Mw of the acid-dissociable group-containing resin (B) not having a branched structure is preferably 1,000-150,000, and particularly preferably 3,000-100,000. The Mw of the acid-dissociable group-containing resin (B) having a branched structure is preferably 5,000-500,000, and particularly preferably 8,000-300,000. The resist obtained from the acid-dissociable group-containing resin (B) having an Mw in the above range possesses excellent development characteristics.

The ratio of Mw to the polystyrene-reduced number molecular weight (hereinafter referred to as "Mn") determined by GPC (Mw/Mn) of the acid-dissociable group-containing resin (B) can be appropriately selected without any restrictions, and is usually 1-10, preferably 1-8, and particularly preferably 1-5. The resist obtained from the acid-dissociable group-containing resin (B) having a Mw/Mn in the above range possesses excellent resolution performance.

There are no restrictions to the method for manufacturing the acid-dissociable group-containing resin (B). As examples of the method for manufacturing, a method of introducing one or more acid-dissociable groups into an acidic functional group of an alkali-soluble resin which has previously been manufactured, a method of polymerizing one or more polymerizable unsaturated monomers having an acid-dissociable group, optionally together with other polymerizable unsaturated monomers, a method of polycondensing one or more polycondensable components having an acid-dissociable group, optionally together with other polycondensable components, and the like can be given.

The polymerization of the polymerizable unsaturated monomers and the polymerization of the one or more polymerizable unsaturated monomers possessing an acid-dissociable group in the manufacture of the alkali soluble resin is carried out by block polymerization, solution polymerization, precipitation polymerization, emulsion polymerization, suspension polymerization, block-suspension polymerization, or the like using an appropriate polymerization initiator or catalyst such as a radical polymerization initiator, anionic polymerization catalyst, coordinated anionic polymerization catalyst, cationic polymerization catalyst, or the like according to the type of polymerizable unsaturated monomer or reaction media.

The polycondensation of the one or more polycondensable components having an acid-dissociable group is preferably carried out in the presence of an acidic catalyst using an aqueous medium or a mixture of water and a hydrophilic solvent.

The amount of the acid generator (A) used in the positive-tone radiation-sensitive resin composition of the present invention can be appropriately selected depending on the desired properties of the resist. The acid generator (A) is preferably used in an amount of 0.001-70 parts by weight, more preferably 0.01-50 parts by weight, and particularly preferably 0.1-20 parts by weight for 100 parts by weight of the acid-dissociable group-containing resin (B). Using the acid generator (A) in an amount of 0.001 parts by weight or more prevents deterioration of the sensitivity and resolution of the resist. Also, using the acid generator (A) in an amount of 70 parts by weight or less prevents deterioration of the applicability and pattern shape of the resist.

Acid Diffusion Controller

An acid diffusion controller is preferably added to the positive-tone radiation-sensitive resin composition of the present invention. The acid diffusion controller controls diffusion of an acid generated from the acid generator (A) upon exposure in the resist film and prevents unfavorable chemical reactions in the unexposed region. Addition of the acid diffusion controller further improves storage stability of the resulting radiation-sensitive resin composition and resolution of the resist. Moreover, addition of the acid diffusion controller prevents the line width of the resist pattern from changing due to changes in the post-exposure delay (PED) between exposure and development, whereby a radiation-sensitive resin composition with remarkably superior process stability can be obtained.

As the acid diffusion controller, nitrogen-containing organic compounds of which the basicity does not change due to exposure or heat treatment during formation of a resist pattern are preferable.

As the above-mentioned nitrogen-containing organic compound, a compound of the following formula (16) (hereinafter called "nitrogen-containing compounds (i)"), a diamino compound having two nitrogen atoms in the molecule (hereinafter called "nitrogen-containing compounds (ii)"), a polyamino compound having three or more nitrogen atoms (hereinafter called "nitrogen-containing compounds (iii)"), a compound containing an amide group, a urea compound, a heterocyclic compound containing a nitrogen atom, and the like can be given.

(16)

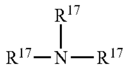

wherein $R^{17}$ individually represents a hydrogen atom, alkyl group, aryl group, or aralkyl group which may be substituted or unsubstituted.

As the substituted or unsubstituted alkyl group in the above formula (16), groups having 1-15 carbon atoms and preferably 1-10 carbon atoms, such as a methyl group, ethyl group, n-propyl group, i-propyl group, n-butyl group, i-butyl group, sec-butyl group, t-butyl group, n-pentyl group, neopentyl group, n-hexyl group, thexyl group, n-heptyl group, n-octyl group, n-ethylhexyl group, n-nonyl group, n-decyl group, and the like can be given.

As examples of the substituted or unsubstituted aryl group, the group having 6-12 carbon atoms such as a phenyl group, tolyl group, xylyl group, cumenyl group, and 1-naphthyl group can be given.

As examples of the substituted or unsubstituted aralkyl group, the group having 7-19 carbon atoms and preferably 7-13 carbon atoms such as a benzyl group, α-methylbenzyl group, phenethyl group, and 1-naphthylmethyl group can be given.

As examples of the nitrogen-containing compounds (i), monoalkylamines such as n-hexylamine, n-heptylamine, n-octylamine, n-nonylamine, and n-decylamine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine; and alkanolamines such as ethanolamine, diethanolamine, and triethanolamine can be given.

As examples of the nitrogen-containing compounds (ii), ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diamino diphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, and the like can be given.

As examples of the nitrogen-containing compound (iii), polyethyleneimine, polyallylamine, a polymer of dimethylaminoethylacrylamide, and the like can be given.

Examples of compounds containing an amide group include formamide, N-methylformamide, N,N-dimethylformamide, acetamide, N-methylacetamide, N,N-dimethylacetamide, propionamide, benzamide, pyrrolidone, and N-methylpyrrolidone.

Examples of urea compounds include urea, methylurea, 1,1-dimethylurea, 1,3-dimethylurea, 1,1,3,3-tetramethylurea, 1,3-diphenylurea, and tributylthiourea.

As examples of the nitrogen-containing heterocyclic compound, imidazoles such as imidazole, benzimidazole, 2-methylimidazole, 4-methylimidazole, 1,2-dimethylimidazole, 2-phenylimidazole, 4-phenylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, 1-piperidine ethanol, 2-piperidine ethanol, morpholine, 4-methylmorpholine, piperazine, 1,4-dimethylpiperazine, 1,4-diazabicyclo[2.2.2]octane, and the like can be given.

A compound having an acid-dissociable group can also be used as the nitrogen-containing organic compound.

As examples of the nitrogen-containing organic compound having an acid-dissociable group, N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, and N-(t-butoxycarbonyl)diphenylamine can be given.

Of these nitrogen-containing organic compounds, the nitrogen-containing compounds (i), nitrogen-containing compounds (ii), nitrogen-containing heterocyclic compounds, and nitrogen-containing organic compounds having an acid-dissociable group are preferable. The acid diffusion controllers may be used either individually or in combination of two or more.

The amount of the acid diffusion controller to be added is preferably 15 parts by weight or less, more preferably 0.001-10 parts by weight, and particularly preferably 0.005-5 parts by weight for 100 parts by weight of the acid-dissociable group-containing resin (B). Incorporating the acid diffusion controller in an amount of 0.001 parts by weight or more prevents deterioration of the pattern shape and size fidelity as a resist. Also, incorporating the acid diffusion controller in an amount of 15 parts by weight or less improves the sensitivity as a resist and improves the developability of the exposure area.

Dissolution Controller

A dissolution controller that improves the solubility in an alkaline developer by the action of an acid may be added to the positive-tone radiation sensitive resin composition of the present invention.

As examples of such a dissolution controller, compounds having an acid functional group such as a phenolic hydroxyl group, carboxyl group, and sulfonic group, compounds in which the hydrogen atom in the acidic functional group is replaced by an acid-dissociable group, and the like can be given.

These dissolution controllers may be used either individually or in combination of two or more. The proportion of the dissolution controllers to be added is 20 parts by weight or less, and preferably 10 parts by weight or less for 100 parts by weight of the total resin component in the radiation-sensitive resin composition.

Surfactant

A surfactant that improves applicability, striation, developability, and the like may be added to the positive-tone radiation sensitive resin composition of the present invention.

As the surfactants, any of anionic surfactants, cationic surfactants, nonionic surfactants, and ampholytic surfactants may be used. Of these, nonionic surfactants are preferable.

As examples of nonionic-type surfactants, polyoxyethylene higher alkyl ethers, polyoxyethylene higher alkyl phenyl ethers, higher fatty acid diesters of polyethylene glycol, commercially available products such as KP (manufactured by Shin-Etsu Chemical Co., Ltd.), Polyflow (manufactured by Kyoeisha Chemical Co., Ltd.), EFTOP (manufactured by Tohkem Products Corporation), MEGAFAC (manufactured by Dainippon Ink and Chemicals, Inc.), Fluorad (manufactured by Sumitomo 3M, Ltd.), Asahi Guard, Surflon (manufactured by Asahi Glass Co., Ltd.), and the like can be given.

These surfactants may be used either individually or in combination of two or more.

The proportion of the surfactants to be added is 2 parts by weight or less, and preferably 1.5 parts by weight or less, as an effective component, for 100 parts by weight of the total resin components in the radiation-sensitive resin composition.

Photosensitizer

A photosensitizer which absorbs radiation energy and transmits the energy to the acid generator (A), thereby increasing the amount of an acid generated upon exposure and further improving the sensitivity may be added to the positive-tone radiation sensitive resin composition of the present invention.

As examples of preferable sensitizers, acetophenones, benzophenones, naphthalenes, biacetyl, eosine, rose bengale, pyrenes, anthracenes, phenothiazines, and the like can be given.

These sensitizers may be used either individually or in combinations of two or more. The proportion of the sensitizers to be added is 50 parts by weight or less, and preferably 30 parts by weight or less for 100 parts by weight of the total resin component in the radiation-sensitive resin composition.

Other Additives

Other additives may be added to the positive-tone radiation sensitive resin composition of the present invention, as required, to the extent that does not impair the effects of the present invention. Examples of such additives include dyes, pigments, adhesion adjuvants, halation inhibitors, preservatives, defoaming agents, and shape improvers. Specific additives include 4-hydroxy-4'-methylchalcone, and the like.

Addition of a dye or a pigment adjusts transmittance of the radiation-sensitive resin composition, thereby decreasing the effects of halation during exposure. Use of an adhesion improver improves adhesion to the substrates.

Preparation of Composition Solution

The positive-tone radiation-sensitive resin composition of the present invention is usually prepared as a composition solution by dissolving the components in a solvent to obtain a homogeneous solution and, optionally, filtering the solution through a filter with a pore size of about 0.2 μm.

Ethers, esters, ether esters, ketones, ketone esters, amides, amide esters, lactams, lactones, and (halogenated) hydrocarbons are given as examples of the solvent which can be used here. Specific examples are ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, acetates, hydroxy acetates, lactates, alkoxy acetates, (non)cyclic ketones, acetoacetates, pyruvates, propionates, N,N-dialkyl formamides, N,N-dialkyl acetamides, N-alkylpyrolidones, γ-lactones, (halogenated) aliphatic hydrocarbons, and (halogenated) aromatic hydrocarbons.

More specifically, such solvents include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, propylene glycol monomethyl ether acetate, propylene glycol monoethyl ether acetate, propylene glycol mono-n-propyl ether acetate, isopropenyl acetate, isopropenyl propionate, toluene, xylene, methyl ethyl ketone, cyclohexanone, 2-heptanone, 3-heptanone, 4-heptanone, ethyl 2-hydroxypropionate, ethyl 2-hydroxy-2-methyl propionate, ethyl ethoxyacetate, ethyl hydroxyacetate, methyl 2-hydroxy-3-methylbutyrate, methyl lactate, ethyl lactate, n-propyl lactate, i-propyl lactate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxy propionate, ethyl 3-methoxypropionate, methyl 3-ethoxypropionate, ethyl 3-ethoxypropionate, N-methyl pyrolidone, N,N-dimethyl formamide, and N,N-dimethyl acetamide.

Of these solvents, propylene glycol monoalkyl ether acetates, 2-heptanone, lactates, 2-hydroxypropionates, 3-alkoxypropionates, and the like are desirable to ensure excellent uniformity of the film surface during application.

These solvents may be used either individually or in combination of two or more.

One or more solvents with a high boiling point may optionally be added to the solvent. Examples of such solvents with a high boiling point include benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

These other solvents may be used either individually or in combination of two or more.

The proportion of the other solvents to be added is 50 wt % or less, and preferably 30 wt % or less of the total amount of solvents used.

The solvents are used in a total amount to make the total solid content of the solution composition usually 5-50 wt %, preferably 10-50 wt %, more preferably 10-40 wt %, and particular preferably 10-30 wt %. An optimal amount is 10-25 wt %. The total solid content in the above ranges is desirable to ensure excellent uniformity of the film surface during application.

Formation of Resist Pattern

A resist pattern is formed from the positive-tone radiation-sensitive resin composition of the present invention by applying the composition solution thus prepared to, for example, substrates such as a silicon wafer or a wafer coated with aluminum using an appropriate application method such as rotational coating, cast coating, and roll coating to form a resist film. Then, after optional heat treatment (hereinafter referred to as "PB"), the resist film is exposed to radiation through a mask with a prescribed pattern.

As radiation that can be used here, deep ultraviolet rays such as a bright line spectrum of a mercury lamp (wavelength: 254 nm), KrF excimer laser (wavelength: 248 nm), ArF excimer laser (wavelength: 193 nm), $F_2$ excimer laser (wavelength: 157 nm), and EUV (wavelength: 13 nm); X-rays such as synchrotron radiation, charged particle rays such as electron beams, and the like can be used according to the types of acid generators (A). Preferable radiations are deep ultraviolet rays and charged particle rays, with particularly preferable radiations being a KrF excimer laser (wavelength: 248 nm), ArF excimer laser (wavelength: 193 nm), and electron beams.

The exposure conditions such as the dose of radiation are appropriately determined according to the composition of the positive-tone radiation-sensitive resin composition, types of additives, and the like.

When forming a resist pattern, post exposure bake (hereinafter called "PEB") which is a heat treatment after exposure is preferable to increase apparent sensitivity of the resist.

PEB is performed at a temperature of 30-200° C., and preferably 50-150° C., although the temperature varies depending on the composition of the radiation-sensitive resin composition, types of additives, and the like.

The resist film after exposure is developed in an alkaline developer to form a predetermined resist pattern.

As the alkaline developer, an alkaline aqueous solution in which one or more alkaline compounds such as an alkaline metal hydroxide, aqueous ammonia, alkylamines, alkanolamines, heterocyclic amines, tetraalkylammonium hydroxides, choline, 1,8-diazabicyclo[5.4.0]-7-undecene, and 1,5-diazabicyclo[4.3.0]-5-nonene are dissolved is used. An aqueous solution of tetraalkylammonium hydroxide is a particularly preferable alkaline developer.

The concentration of the alkaline aqueous solution is preferably 10 wt % or less, more preferably 1-10 wt %, and particularly preferably 2-5 wt %. The concentration of the alkaline aqueous solution less than 10 wt % prevents dissolution of an unexposed area in the developer.

The addition of an appropriate amount of a surfactant to the alkaline developer is desirable to increase wettability of the resist to the developer.

The resist film is generally washed with water after development using the alkaline developer.

EXAMPLES

The embodiments of the present invention are described in more detail by examples. However, these examples should not be construed as limiting the present invention.

Synthesis of Sulfonium Salt Compound (1)

Example 1

20 g of 2-naphthalene thiol was dissolved in 100 ml of acetone, and 13.39 g of 4-chloro-1-butanol and 25.04 g of triethylamine were added dropwise. The mixture was reacted for 12 hours at room temperature while stirring and poured into 100 ml of water. The reaction mixture was extracted three times with 50 ml of ethyl acetate. The resulting organic layer was washed three times with 50 ml of 10 wt % sodium carbonate aqueous solution and three times with 50 ml of 5 wt % oxalic-acid aqueous solution. The separated water layer was repeatedly washed with distilled water until pH 7. The organic layer was dried using 3 g of magnesium sulfate. After removing magnesium sulfate by filtration, the solvent was evaporated using a rotary evaporator to obtain 20.2 g of 4-(naphthalen-2-ylsulfanyl)butan-1-ol as a highly viscous oily liquid.

Next, 20.2 g of the 4-(naphthalen-2-ylsulfanyl)butan-1-ol was dissolved in 120 ml of dichloromethane and 17.3 g of triethylamine was added to the solution. After cooling in an ice water bath at 0° C., 11.78 g of methanesulfonyl chloride was added dropwise over five minutes. The mixture was reacted for 15 minutes in an ice water bath and poured into 100 ml of ice water. The organic layer was washed two times with 70 ml of 10 wt % sodium hydrogen carbonate aqueous solution and three times with 5 wt % oxalic-acid aqueous solution. The separated water layer was repeatedly washed with distilled water until pH 7. The organic layer was dried using 5 g of magnesium sulfate. After removing magnesium sulfate by filtration, the solvent was evaporated using a rotary evaporator to obtain 22.0 g of 4-[(naphthalen-2-yl) sulfanyl]butyl ester of methansulfonic acid as a colorless liquid.

22.0 g of the 4-[(naphthalen-2-yl)sulfanyl]butyl ester of methansulfonic acid was dissolved in 100 ml of acetonitrile and the mixture was reacted for 14 hours while heating over a hot water bath at 70° C. The reaction mixture was powered into 100 ml of water, acetonitrile was evaporated using a rotary evaporator, and the residue was washed three times with 30 ml of diethyl ether to obtain 100 g of an aqueous solution of 1-(naphthalen-2-yl)tetrahydrothiophenium methane sulfonate. 40 g of a previously prepared 30 wt % aqueous solution of ammonium nonafluoro-n-butane sulfonate was added dropwise to the resulting aqueous solution. The precipitate was collected by filtration and dried under vacuum to obtain 28.6 g of 1-(naphthalen-2-yl)tetrahydrothiophenium nonafluoro-n-butane sulfonate.

The structure of this compound was identified using fast atom bombardment (FAB) mass spectrometry and $^1$H-NM analysis. FIG. 1 shows the $^1$H-NMR spectrum of this compound. The compound is herein indicated as "sulfonium salt (A-1)".

Example 2

9 g of dichloromethane and 1.0 g of sodium 2-(bicyclo [2.2.1]heptan-2-yl)-1,1,2,2-tetrafluoroethane sulfonate were added to 10 g of an aqueous solution of 1-(naphthalen-2-yl)tetrahydrothiopheniummethane sulfonate which was synthesized in the same manner as the sulfonium salt (A-1). The mixture was reacted while vigorously stirring for 12 hours using a magnetic stirrer. After the reaction, 10 g of dichloromethane was added. The organic layer was washed five times with 10 g of water and dried using 2 g of magnesium sulfate. The magnesium sulfate was then removed by filtration. The solvent was evaporated using a rotary evaporator to obtain 1.4 g of 1-(naphthalen-2-yl)tetrahydrothiophenium 2-(bicyclo[2.2.1]heptan-2-yl)-1,1,2,2-tetrafluoroethane sulfonate as a white solid.

Figure 2:
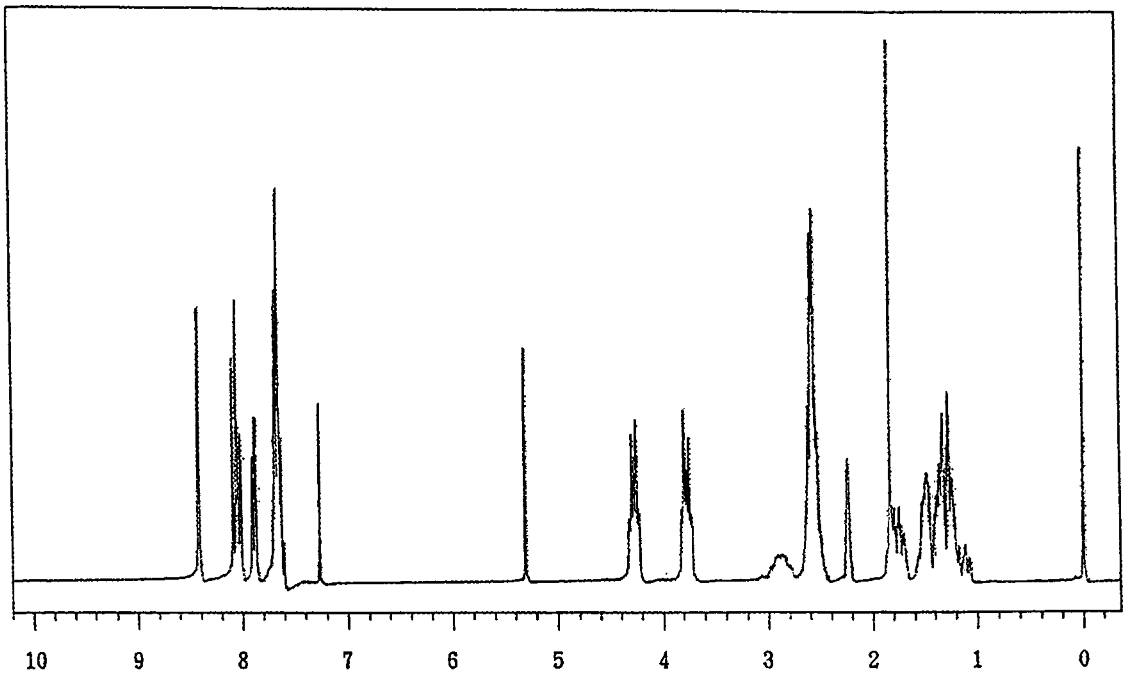
FIG. 2 shows a $^1$H-NMR spectrometry spectrum of the sulfonium salt (A-2).

The structure of this compound was identified using fast atom bombardment (FAB) mass spectrometry and $^1$H-NMR analysis. FIG. 2 shows the $^1$H-NMR spectrum of this compound. The compound is herein indicated as "sulfonium salt (A-2)".

Example 3

6.0 g of 1-(naphthalen-2-yl)tetrahydrothiophenium methane sulfonate synthesized in the same manner as in Example 1 was added dropwise to 5.0 g of previously prepared 30 wt % methanol solution of perfluoro-n-octane sulfonic acid. After the addition, the reaction solution was poured into 50 g of water. White precipitate was collected by filtration, washed several times with water, and dried under vacuum to obtain 2.1 g of 1-(naphthalen-2-yl)tetrahydrothiophenium perfluoro-n-octane sulfonate as a white solid.

Figure 3:
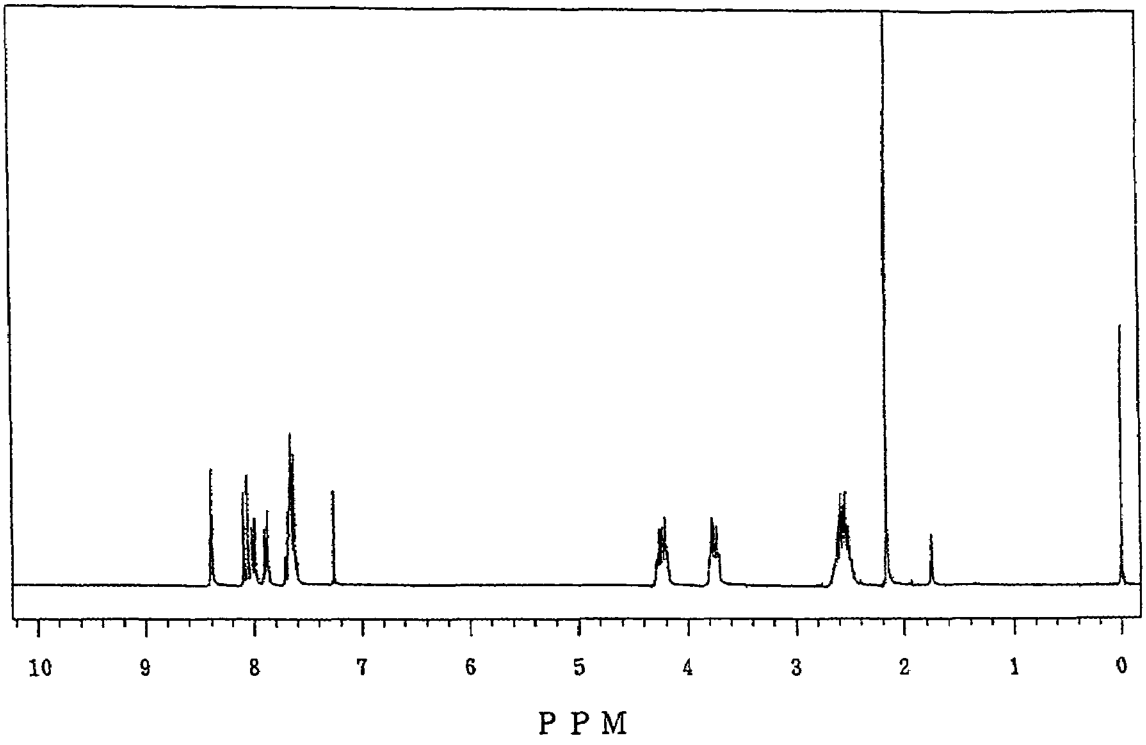
FIG. 3 shows a $^1$H-NMR spectrometry spectrum of the sulfonium salt (A-3).

The structure of this compound was identified using fast atom bombardment (FAB) mass spectrometry and $^1$H-NMR analysis. FIG. 3 shows the $^1$H-NMR spectrum of this compound. The compound is herein indicated as "sulfonium salt (A-3)".

Example 4

The method described in Japanese Patent Application Laid-open No. 2002-229192 was followed using 5-norbornen-2-endo-3-endo-dimethanol as a starting material to obtain 4.5 g of corresponding norbornanedimethylene sulfoxide.

4.5 g of the norbornanedimethylene sulfoxide was placed in a 500 ml eggplant flask and dissolved in 100 ml of tetrahydrofuran. The solution was cooled in a dry-ice acetone bath at −78° C. and 5.4 ml of trimethylsilyltrifluoromethane sulfonate was added, followed by continued stirring for one hour. Stirring was continued for a further 1.5 hours at a bath temperature of −40° C. After decreasing the bath temperature to −78° C., 100 ml of a previously prepared solution of 0.5 mol of 2-naphthyl magnesium bromide in 1 l of tetrahydrofuran was added dropwise. The mixture was stirred at the same temperature for one hour. The reaction solution was poured into 500 ml of 5 wt % aqueous solution of trifluoromethansulfonic acid and tetrahydrofuran was evaporated using a rotary evaporator. 100 ml of chloroform was added to the residue to extract a reaction product. The chloroform layer was washed three times with 100 ml of 5 wt % aqueous solution of trifluoromethansulfonic acid and dried using anhydrous magnesium sulfate, which was then removed by filtration. Chloroform was evaporated using a rotary evaporator, the residue was dried under reduced pressure, and purified by column chromatography (developing solvent: dichloromethane) to obtain 4.1 g of a salt of trifluoromethane sulfonate having a cation moiety of the following formula (17).

(17)

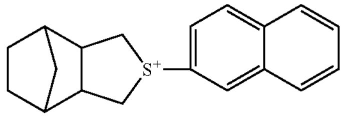

4.1 g of the trifluoromethane sulfonate salt was replaced with chloride salt using 60 g of anion exchange column (A25) to which the chlorine anion was adsorbed with ammonium chloride. The chloride salt was dissolved in 50 ml of water and reacted with 45 ml of 30 wt % ammonium nonafluoro-n-butane sulfonate aqueous solution, which was previously prepared from nonafluoro-n-butane sulfonic acid and ammonia. The resulting precipitate was collected by filtration and dried to obtain 4.4 g of nonafluoro-n-butane-sulfonate having a cation moiety of the formula (17).

Figure 4:
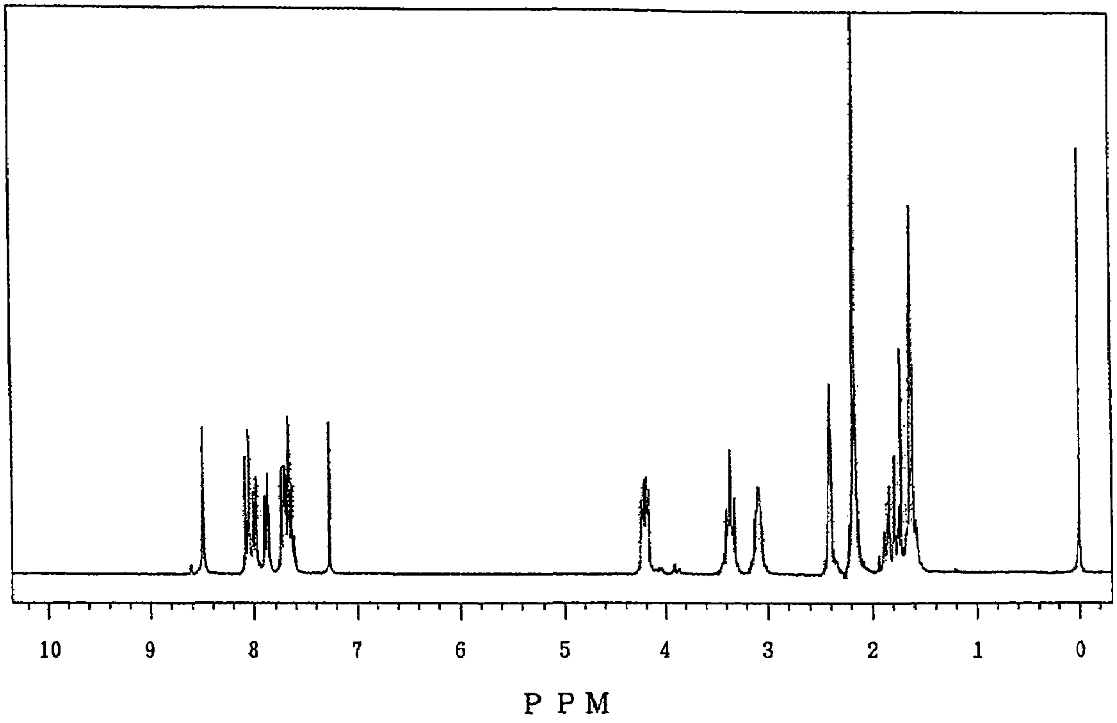
FIG. 4 shows a $^1$H-NMR spectrometry spectrum of the sulfonium salt (A-4).

The structure of this compound was identified using fast atom bombardment (FAB) mass spectrometry and $^1$H-NMR analysis. FIG. 4 shows the $^1$H-NMR spectrum of this compound. The compound is herein indicated as "sulfonium salt (A-4)".

Example 5

9.464 g of tetramethylene sulfoxide was dissolved in 200 ml of dichloromethane. After cooling the solution to −78° C., 16.7 g of bromotrimethyl silane was added dropwise. The mixture was then heated to −50° C. and stirred for one hour. After cooling the resulting solution to −78° C., a tetrahydrofuran solution of 6-n-butoxy-2-naphthyl magnesium bromide prepared from 38 g of 2-bromo-6-n-butoxy naphthalene, 3.65 g of magnesium, and 263 ml of tetrahydrofuran according to the method described in J. Am. Chem.

Soc., Vol. 118, P. 6841-6852 (1996) was added dropwise over one hour. After increasing the reaction temperature to −50° C., the mixture was reacted for one hour. Then, 750 ml of 10 wt % hydrobromic acid aqueous solution was added to terminate the reaction. The organic solvent was evaporated using a rotary evaporator. Insoluble components were extracted three times with 200 ml of diethyl ether and 100 ml of 30 wt % ammonium nonafluoro-n-butane sulfonate aqueous solution was added dropwise to the water layer while stirring. The resulting precipitate was filtered, washed with distilled water, and dried using a vacuum pump to obtain 10.4 g of 1-(6-n-butoxynaphthalen-2-yl)tetrahydrothiophenium nonafluoro-n-butane sulfonate as a white solid.

Figure 5:
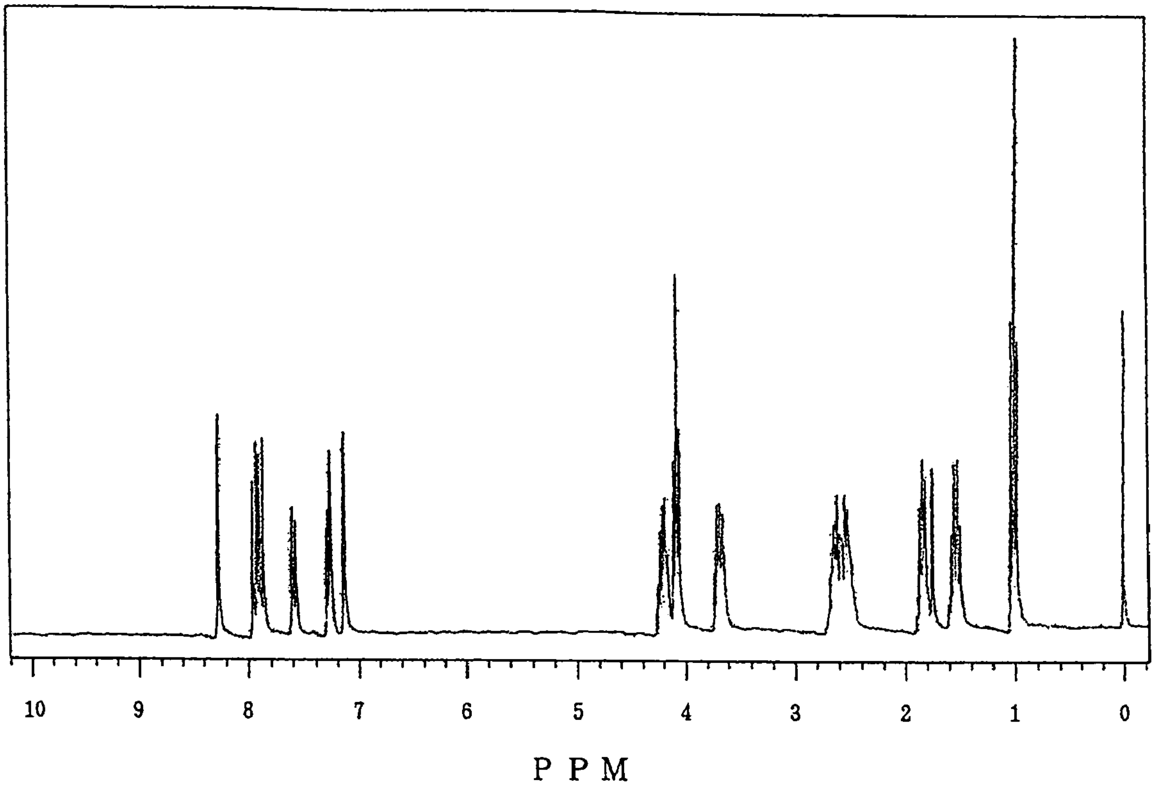
FIG. 5 shows a $^1$H-NMR spectrometry spectrum of the sulfonium salt (A-5).

The structure of this compound was identified using fast atom bombardment (FAB) mass spectrometry and $^1$H-NMR analysis. FIG. 5 shows the $^1$H-NMR spectrum of this compound. The compound is herein indicated as "sulfonium salt (A-5)".

Example 6

30 g 6-n-butoxy-2-naphthalene thiol was obtained by the method of non-patent document 5 from 72 g of 2-bromo-6-n-butoxy naphthalene prepared according to the method described in J. Am. Chem. Soc., Vol. 118, P. 6841-6852 (1996) and 6-n-butoxy-2-naphthyl magnesium bromide prepared from 7.5 g of magnesium. Next, 30 g of 6-n-butoxy-2-naphthalene thiol was dissolved in 150 ml of acetone and 14.0 g of 4-chloro-1-butanol was added to the solution. After the addition of 26.1 g of triethylamine dropwise over 15 minutes, the mixture was reacted for 15 hours at room temperature while stirring. Next, 150 ml of ethyl acetate and 150 ml of water were added to the reaction mixture. After removing the water layer using a separating funnel, the organic layer was washed three times with 75 ml of a 10 wt % sodium carbonate aqueous solution, then repeatedly washed with 5 wt % oxalic acid aqueous solution until the water layer becomes pH 2. Then, the organic layer was washed with purified water until the water layer becomes pH 7 and dried using magnesium sulfate. After drying, magnesium sulfate was removed by filtration and the solvent was evaporated using a rotary evaporator at 40° C. under reduced pressure by a stream aspirator to obtain 29.4 g of 4-hydroxybutyl-(6-n-butoxynaphthalen-2-yl)sulfide, of which the purity determined by high performance liquid chromatography (HPLC) was 95 wt % or more.

29.4 g of 4-hydroxybutyl-(6-n-butoxynaphthalen-2-yl) sulfide thus obtained was dissolved in 180 ml of dichloromethane. After cooling to −5° C. over an ice saturated brine bath, 13.3 g of methanesulfonyl chloride was added. Then, 19.6 g triethylamine was added dropwise over 15 minutes while controlling the temperature at less than 0° C. After reacting for one hour at 0-5° C., 100 ml of ice water was added and the resulting mixture was stirred for five minutes. The water layer was removed using a separating funnel. The organic layer was washed twice with 70 ml of 10 wt % sodium hydrogencarbonate aqueous solution and three times with 70 ml of 5 wt % oxalic acid aqueous solution. Then, the organic layer was washed with purified water until the water layer becomes pH 7 and dried using magnesium sulfate. After drying, magnesium sulfate was removed by filtration and the solvent was evaporated using a rotary evaporator at room temperature under reduced pressure by a stream aspirator to obtain 33 g of crude product of 4-methanesulfonyloxybutyl-(6-n-butoxynaphthalen-2-yl)sulfide, of which the purity determined by HPLC was 93 wt %. The crude product contained 5 wt % of 1-(6-n-butoxynaphthalen-2-yl)tetrahydrothiophenium methane sulfonate.

33 g of crude product of 4-methanesulfonyloxybutyl-(6-n-butoxynaphthalen-2-yl)sulfide thus obtained was mixed with 150 g of acetonitrile. After heating to 70° C. over an oil bath, the mixture was reacted for 14 hours with stirring. The reaction mixture was poured into 100 g of water and acetonitrile was evaporated using a rotary evaporator at 40° C. under reduced pressure by a stream aspirator. The residue was extracted three times with 50 ml of diethyl ether to remove water-insoluble components, thereby obtaining an aqueous solution of 1-(6-n-butoxynaphthalen-2-yl)tetrahydrothiophenium methane sulfonate, of which the purity determined by HPLC was 98 wt % or more.

100 ml of dichloromethane and 28.61 g of sodium 2-(bicyclo[2.2.1]heptan-2-yl)tetrafluoroethane sulfonate were added to the aqueous solution of 1-(6-n-butoxynaphthalen-2-yl)tetrahydrothiophenium methane sulfonate and the mixture was stirred for 12 hours. After removing the water layer using a separating funnel, the organic layer was washed five times with 40 ml of purified water. The solvent was evaporated using a rotary evaporator under reduced pressure by a stream aspirator at room temperature and the residue was dried at 50° C. under reduced pressure to obtain 24.2 g of 1-(6-n-butoxynaphthalen-2-yl)tetrahydrothiophenium 2-(bicyclo[2.2.1]heptan-2-yl)tetrafluoroethane sulfonate as a white solid.

Figure 6:
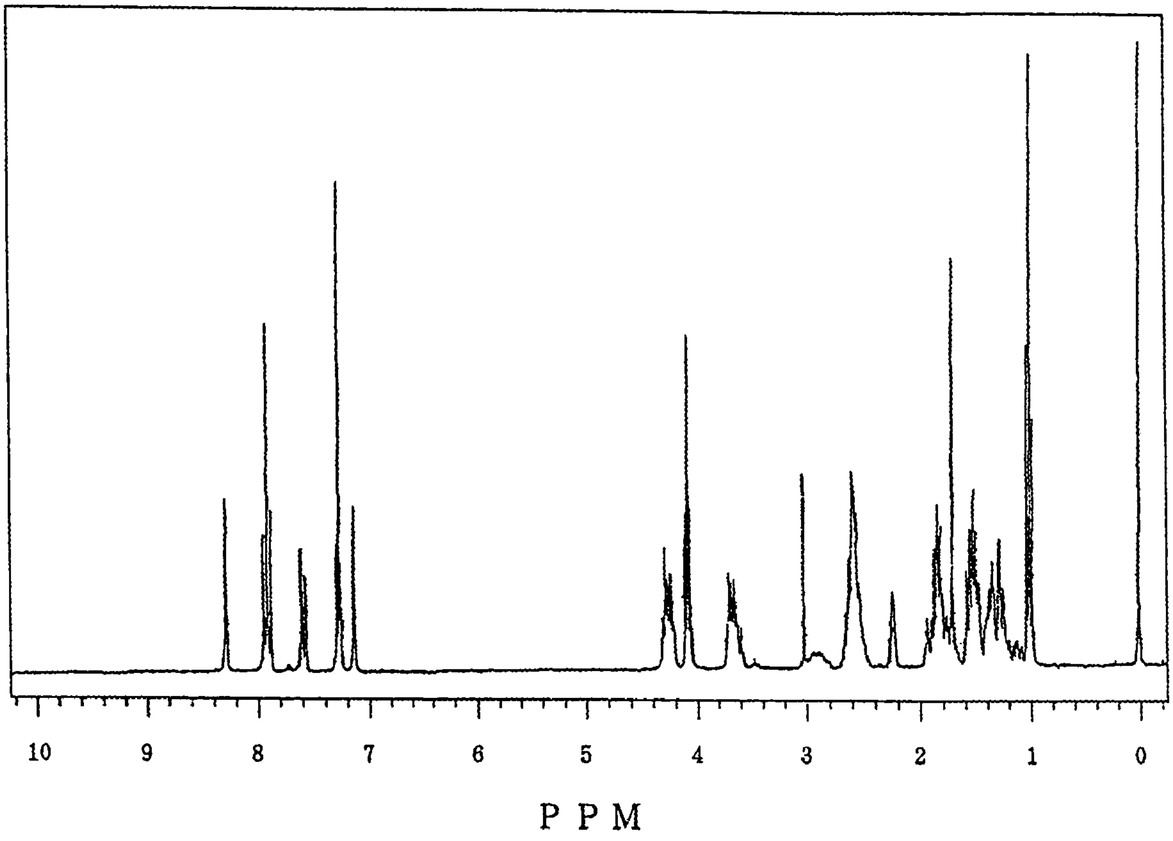
FIG. 6 shows a $^1$H-NMR spectrometry spectrum of the sulfonium salt (A-6).

The structure of this compound was identified using fast atom bombardment (FAB) mass spectrometry, $^1$H-NMR analysis, and $^{19}$F-NMR analysis. FIG. 6 shows the $^1$H-NMR spectrum of this compound. The compound is herein indicated as "sulfonium salt (A-6)".

(Measurement of Molar Extinction Coefficient)

Sulfonium salts (A-1) to (A-5) were dissolved in acetonitrile to prepare solutions with a concentration of $5.0\times10^{-4}$ mmol/liter. Absorption spectra of these solutions were measured using a quartz cell with an exposure length of 10 mm by an ultraviolet-visible region spectrophotometer (V550 manufactured by Jasco Corp.).

Absorption spectra of the following sulfonium salts (a-1) to (a-3) were also measured in the same manner.

The molar extinction coefficient of each sulfonium salt at a wavelength of 193 nm was calculated from the resulting absorption spectrum. The results are shown in Table 1.

Sulfonium salt (a-1): 1-(4-fluoronaphthalen-1-yl)tetrahydrothiophenium nonafluoro-n-butane sulfonate Sulfonium salt (a-2): 1-(4-n-butoxynaphthalen-1-yl)tetrahydrothiophenium nonafluoro-n-butane sulfonate Sulfonium salt (a-3): Triphenylsulfonium nonafluoro-n-butanesulfonate

TABLE 1

| Sulfonium salt | Molar extinction coefficient at a wavelength of 193 nm (l/mol · cm) |
|---|---|
| A-1 | 10,600 |
| A-2 | 10,650 |
| A-3 | 10,620 |
| A-4 | 8,990 |
| A-5 | 7,900 |
| A-6 | 7,920 |
| a-1 | 14,120 |
| a-2 | 21,540 |
| a-3 | 26,600 |

As is clear from Table 1, the sulfonium salt compounds (I) of the present invention were confirmed to have small absorption at a wavelength of 193 nm and high transparency to an ArF excimer laser as compared with conventional sulfonium salt compounds.

Examples 7-18 and Comparative Example 1

(Performance Evaluation of Positive-tone Radiation Sensitive Resin Composition)

Components shown in Table 2 (part(s) indicates part(s) by weight) were mixed to prepare homogeneous solutions. The solutions were filtered through a membrane filter with a pore diameter of 0.2 μm to prepare solution compositions.

Each composition solution was applied to a silicon wafer, coated with an antireflection film (ARC) as a lower layer membrane, by spin coating to obtain a resist film with a thickness of 0.34 μm, followed by baking (PB) on a hot plate at 130° C. for 90 seconds. The resist film was exposed to an ArF excimer laser using an apparatus manufactured by Nikon Corp. (numerical aperture 0.55), baked (PEB) on a hot plate at 130° C. for 90 seconds, developed in a 2.38 wt % aqueous solution of tetramethylammonium hydroxide for one minute, washed with water, and dried to form a resist pattern.

The resist film performance was evaluated on the following items according to the methods described below. The evaluation results are shown in Table 3.

Sensitivity: An optimum dose capable of forming a 1:1 line width from a line-and-space (1L1S) pattern with a line width of 0.15 μm was taken as sensitivity.

Resolution: The minimum line and space (1L1S) dimension resolved by an optimum dose of irradiation was taken as the resolution.

Pattern shape: The cross-section of a line-and-space (1L1S) pattern with a line width of 0.15 μm was measured by a scanning electron microscope.

LER: A resist pattern was formed by irradiating a sample with light at a dose reproducing a line and space pattern (1L1S) with a line width of0.15 μm. The surface of one side of the pattern edge was inspected at two or more positions using a scanning electron microscope (SEM) to calculate 3σ dispersion in the direction perpendicular to the direction of the pattern lines. The LER was evaluated according to the following standard.

○: 3σ dispersion is less than 8 nm.

Δ: 3σ dispersion is 8 nm or more, but less than 10 nm.

×: 3σ dispersion is 10 nm or more.

Storage stability: Each composition solution was stored at 20° C. for three months to measure sensitivity immediately after preparation, after one month of storage, and after three months of storage. The storage stability was evaluated according to the following standard.

○: Sensitivity change after three months of storage is less than 3%.

×: Sensitivity change after three months of storage is 3% or more.

The components in Table 2 other than those described above are as follows.

(B) Acid-dissociable Group-containing Resin

B-1: Copolymer in which the ratio of the recurring unit of the formula (10-15) ($R^{11}$=methyl group, hereinafter the same) and the recurring unit of the formula (11-1) ($R^{13}$=methyl group, hereinafter the same) is 40:60 (Mw=9,000)

B-2: Copolymer in which the ratio of the recurring unit of the formula (10-15), the recurring unit of the formula (11-1), and the recurring unit of the formula (12-1) ($R^{15}$=methyl group, hereinafter the same) is 45:30:25 (Mw=9,000)

B-3: Copolymer in which the ratio of the recurring unit of the formula (10-17) ($R^{11}$=methyl group, hereinafter the same) and the recurring unit of the formula (11-1) is 40:60 (Mw=6,000)

B-4: Copolymer in which the ratio of the recurring unit of the formula (10-17), the recurring unit of the formula (11-1), and the recurring unit of the formula (12-1) is 45:30:25 (Mw=7,000)

Photoacid Generator

A-1: Sulfonium salt (A-1).

A-2: Sulfonium salt (A-2).

A-3: Sulfonium salt (A-3).

A-4: Sulfonium salt (A-4).

A-5: Sulfonium salt (A-5).

A-6: Sulfonium salt (A-6).

a-1: 1-(2-oxo-n-butyl)tetrahydrothiophenium nonafluoro-n-butanesulfonate

Acid Diffusion Controller

C-1: 2-Phenylbenzimidazole

C-2: N-t-butoxycarbonyl-2-phenylbenzimidazole

Dissolution Controller

D-1: t-Butyl deoxycholate

Solvent

S-1: Propylene glycol monomethyl ether acetate

S-2: γ-Butyrolactone

TABLE 2

| | Photoacid generator (part by weight) | Acid-dissociable group-containing resin (B) (part by weight) | Acid diffusion controller (part by weight) | Dissolution controller (part by weight) | Solvent (part by weight) |
|---|---|---|---|---|---|
| Example 7 | A-1 (5) | B-1 (100) | C-1 (0.25) | | S-1 (700)<br>S-2 (35) |
| Example 8 | A-1 (5) | B-2 (100) | C-1 (0.25) | | S-1 (700)<br>S-2 (35) |
| Example 9 | A-1 (5) | B-3 (100) | C-1 (0.25) | | S-1 (700)<br>S-2 (35) |
| Example 10 | A-1 (5) | B-4 (100) | C-1 (0.25) | | S-1 (700)<br>S-2 (35) |
| Example 11 | A-2 (5) | B-2 (100) | C-1 (0.25) | | S-1 (700)<br>S-2 (35) |

TABLE 2-continued

| | Photoacid generator (part by weight) | Acid-dissociable group-containing resin (B) (part by weight) | Acid diffusion controller (part by weight) | Dissolution controller (part by weight) | Solvent (part by weight) |
|---|---|---|---|---|---|
| Example 12 | A-3 (5) | B-2 (100) | C-1 (0.25) | | S-1 (700) S-2 (35) |
| Example 13 | A-1 (5) | B-1 (90) | C-2 (0.25) | D-1 (10) | S-1 (700) S-2 (35) |
| Example 14 | A-1 (8) | B-2 (100) | C-1 (0.40) | | S-1 (700) S-2 (35) |
| Example 15 | A-1 (8) | B-2 (100) | C-1 (0.40) | | S-1 (700) S-2 (35) |
| Example 16 | A-5 (8) | B-2 (100) | C-1 (0.40) | | S-1 (700) S-2 (35) |
| Example 17 | A-4 (5) | B-2 (100) | C-1 (0.25) | | S-1 (700) S-2 (35) |
| Example 18 | A-6 (8) | B-2 (100) | C-1 (0.40) | | S-1 (700) S-2 (35) |
| Comparative Example 1 | a-1 (8) | B-2 (100) | C-1 (0.25) | | S-1 (700) S-2 (35) |

TABLE 3

| | Sensitivity ($J/m^2$) | Resolution (μm) | Pattern profile | LER | Storage stability |
|---|---|---|---|---|---|
| Example 7 | 350 | 0.13 | Rectangle | Δ | ○ |
| Example 8 | 300 | 0.12 | Rectangle | Δ | ○ |
| Example 9 | 280 | 0.13 | Rectangle | Δ | ○ |
| Example 10 | 250 | 0.12 | Rectangle | Δ | ○ |
| Example 11 | 370 | 0.12 | Rectangle | Δ | ○ |
| Example 12 | 330 | 0.13 | Rectangle | Δ | ○ |
| Example 13 | 350 | 0.12 | Rectangle | ○ | ○ |
| Example 14 | 220 | 0.12 | Rectangle | ○ | ○ |
| Example 15 | 235 | 0.13 | Rectangle | ○ | ○ |
| Example 16 | 210 | 0.12 | Rectangle | ○ | ○ |
| Example 17 | 250 | 0.12 | Rectangle | ○ | ○ |
| Example 18 | 220 | 0.12 | Rectangle | ○ | ○ |
| Comparative Example 1 | 650 | 0.15 | Rectangle | X | X |

As can be seen from Table 3, the positive-tone radiation sensitive resin composition using the acid generator (A1) of the present invention excels in storage stability and base resistance, is highly sensitive, and has a high resolution as compared with the composition of the Comparative Example 1 in which the acid generator (A1) is not used.

INDUSTRIAL APPLICABILITY

The sulfonium salt compound (I) of the present invention has high transparency to deep ultraviolet rays with a wavelength of 220 nm or less and excels in base resistance, and when used as a photoacid generator in a chemically-amplified photoresist to be exposed to deep ultraviolet rays, a resist composition with excellent sensitivity, resolution, pattern shape, LER, storage stability, and the like can be obtained.

Therefore, the positive-tone radiation-sensitive resin composition using the photoacid generator containing the sulfonium salt compound (I) as an essential component is extremely useful as a chemically-amplified resist for manufacturing semiconductor devices, which will become more and more miniaturized in the future.

The invention claimed is:

1. A sulfonium salt compound shown by the following formula (1), (I)

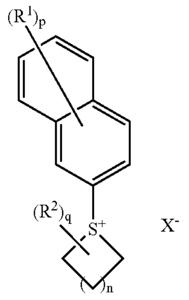

wherein $R^1$ represents a linear or branched alkyl group having 1-14 carbon atoms, a monovalent hydrocarbon group having an alicyclic skeleton and containing 3-14 carbon atoms, a linear or branched alkoxyl group having 1-14 carbon atoms, a group represented by $—OR^3$ (wherein $R^3$ is a monovalent hydrocarbon group having an alicyclic skeleton and containing 3-14 carbon atoms), a linear or branched alkyl sulfanyl group having 1-14 carbon atoms, an organic sulfanyl group having an alicyclic skeleton and containing 3-14 carbon atoms, a linear or branched alkane sulfonyl group having 1-14 carbon atoms, or an organic sulfonyl group having an alicyclic skeleton and containing 3-14 carbon atoms, two or more $R^1$ being either the same or different, $R^2$ represents a substituted or unsubstituted, linear, branched, or cyclic alkyl group having 1-14 carbon atoms, or two or more $R^2$ groups bond to form a monocyclic structure having 3-14 carbon atoms or a polycyclic structure having 6-14 carbon atoms, two or more $R^2$ groups being either the same or different, p is an integer of 0-7, q is an integer of 0-6, n is an integer of 0-3, and $X^-$ represents a sulfonic acid anion.

2. The sulfonium-salt compound according to claim 1, wherein the group $X^-$ in the formula (1) is a sulfonic-acid anion of the following formula (II), $$R^4—CF_2CF_2SO_3^- \qquad (II)$$

wherein $R^4$ represents a substituted or unsubstituted, linear or branched alkyl group having 1-14 carbon atoms or a substituted or unsubstituted, monovalent hydrocarbon group having an alicyclic ring and containing 3-14 carbon atoms.

3. The sulfonium-salt compound according to claim 1, wherein p is 0 or 1, q is 0, and n is 2 in the formula (I).

4. The sulfonium-salt compound according to claim 1, wherein p is 1, q is 0, n is 2, and $R^1$ is a linear or branched alkoxyl group having 1-14 carbon atoms in the formula (I).

5. The sulfonium-salt compound according to claim 1, wherein p is 1, q is 0, n is 2, and $R^1$ represents —$OR^3$ (wherein $R^3$ is a monovalent hydrocarbon group having an alicyclic skeleton and containing 3-14 carbon atoms) in the formula (I).

6. The sulfonium-salt compound according to claim 1, having a molar extinction coefficient at a wavelength of 193 nm of 10,650 l/mol·cm or less.

7. A photoacid generator comprising the sulfonium salt compound according to claim 1.

8. A positive-tone radiation-sensitive resin composition comprising (A) a photoacid generator comprising the photoacid generator according to claim 7 and (B) an acid-dissociable group-containing resin which is insoluble or scarcely soluble in alkali and becomes alkali soluble when the acid-dissociable group dissociates.

9. The positive-tone radiation-sensitive resin composition according to claim 8, wherein the resin of the component (B) has a recurring unit of the following formula (10), (10)

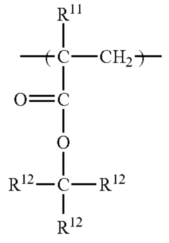

wherein $R^{11}$ represents a hydrogen atom or methyl group and $R^{12}$ individually represents a linear or branched alkyl group having 1-4 carbon atoms or a substituted or unsubstituted monovalent alicyclic hydrocarbon group having 3-20 carbon atoms, or any two of $R^{12}$ groups form, in combination and together with the carbon atom with which these groups bond, a substituted or unsubstituted, bridged or unbridged, divalent alicyclic hydrocarbon group having 3-20 carbon atoms, with the remaining $R^{12}$ group being a linear or branched alkyl group having 1-4 carbon atoms or a substituted or unsubstituted monovalent alicyclic hydrocarbon group having 3-20 carbon atoms.

10. The positive-tone radiation-sensitive resin composition according to claim 8, wherein the amount of the acid-dissociable groups introduced into the resin (B) is 5-100%.

11. The positive-tone radiation-sensitive resin composition according to claim 9, wherein any two of the $R^{12}$ groups, in the recurring unit of the formula (10) in the resin (B), form, in combination and together with the carbon atom with which these groups bond, a substituted or unsubstituted, bridged or unbridged, divalent alicyclic hydrocarbon group having 3-20 carbon atoms, with the remaining $R^{12}$ group being a linear or branched alkyl group having 1-4 carbon atoms.

12. The positive-tone radiation-sensitive resin composition according to claim 9, wherein any two of the $R^{12}$ groups, in the recurring unit of the formula (10) in the resin (B), form, in combination and together with the carbon atom with which these groups bond, a substituted or unsubstituted, bridged or unbridged, divalent alicyclic hydrocarbon group having 3-20 carbon atoms and the remaining $R^{12}$ group is a linear alkyl group having 1-4 carbon atoms.

13. The positive-tone radiation-sensitive resin composition according to claim 8, wherein the resin of the component (B) has a polystyrene-reduced weight molecular weight determined by gel permeation chromatography of 1,000 to 500,000.

14. The positive-tone radiation-sensitive resin composition according to claim 8, wherein the resin of the component (B) has a ratio (Mw/Mn) of the polystyrene-reduced weight molecular weight (Mw) to the polystyrene-reduced number average molecular weight (Mn) determined by gel permeation chromatography (GPC) of the resin (B) of 1-5.

15. The positive-tone radiation-sensitive resin composition according to claim 8, wherein the content of the component (A) is 0.001-70 parts by weight for 100 parts by weight of the component (B).

16. The sulfonium-salt compound according to claim 2, wherein p is 0 or 1, q is 0, and n is 2 in the formula (I).

17. The sulfonium-salt compound according to claim 2, wherein p is 1, q is 0, n is 2, and $R^1$ is a linear or branched alkoxyl group having 1-14 carbon atoms in the formula (I).

18. The sulfonium-salt compound according to claim 2, wherein p is 1, q is 0, n is 2, and $R^1$ represents —$OR^3$ (wherein $R^3$ is a monovalent hydrocarbon group having an alicyclic skeleton and containing 3-14 carbon atoms) in the formula (I).

19. The sulfonium-salt compound according to claim 2, having a molar extinction coefficient at a wavelength of 193 nm of 10,650 l/mol·cm or less.

20. A sulfonium salt compound shown by the following formula (1), (I)

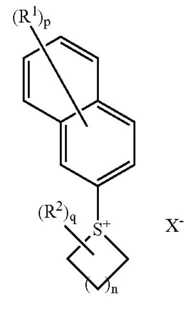

wherein $R^1$ represents a linear or branched alkyl group having 1-14 carbon atoms, a monovalent hydrocarbon group having an alicyclic skeleton and containing 3-14 carbon atoms, a linear or branched alkoxyl group having 1-14 carbon atoms, a group represented by —$OR^3$ (wherein $R^3$ is a monovalent hydrocarbon group having an alicyclic skeleton and containing 3-14 carbon atoms), a linear or branched alkyl sulfanyl group having 1-14 carbon atoms, an organic sulfanyl group having an alicyclic skeleton and containing 3-14 carbon atoms, a linear or branched alkane sulfonyl group having 1-14 carbon atoms, or an organic sulfonyl group having an alicyclic skeleton and containing 3-14 carbon atoms, two or more $R^1$ being either the same or different, $R^2$ represents a substituted or unsubstituted, linear, branched, or cyclic alkyl group having 1-14 carbon atoms, or two or more $R^2$ groups bond to form a monocyclic structure having 3-14 carbon atoms or a polycyclic structure having 6-14 carbon atoms, two or more $R^2$ groups being either the same or different, p is an integer of 0-7, q is 0, n is an integer of 0-3, and $X^-$ represents a sulfonic acid anion.

* * * * *